United States Patent
Goble

(10) Patent No.: US 7,278,994 B2
(45) Date of Patent: Oct. 9, 2007

(54) ELECTROSURGICAL INSTRUMENT

(75) Inventor: Nigel M. Goble, Hungerford (GB)

(73) Assignee: Gyrus Medical Limited, Cardiff (GB)

( * ) Notice: Subject to any disclaimer, the term of this patent is extended or adjusted under 35 U.S.C. 154(b) by 225 days.

(21) Appl. No.: 10/656,877

(22) Filed: Sep. 8, 2003

(65) Prior Publication Data

US 2004/0102770 A1    May 27, 2004

Related U.S. Application Data

(63) Continuation-in-part of application No. 10/437,431, filed on May 14, 2003, now abandoned, which is a continuation of application No. 09/462,927, filed as application No. PCT/GB98/02094 on Jul. 15, 1998, now Pat. No. 6,565,560, application No. 10/656,877, and a continuation-in-part of application No. 10/036,500, filed on Jan. 7, 2002, now Pat. No. 6,923,803, which is a continuation-in-part of application No. 10/024,348, filed on Dec. 21, 2001, now abandoned, which is a continuation-in-part of application No. 09/484,225, filed on Jan. 18, 2000, now Pat. No. 6,336,926.

(30) Foreign Application Priority Data

| Jul. 18, 1997 | (GB) | ................................. 9715200.3 |
| Dec. 19, 1997 | (GB) | ................................. 9726952.6 |
| Jul. 7, 1998 | (GB) | ................................. 9814727.5 |
| Jan. 15, 1999 | (GB) | ................................. 9900964.9 |

(51) Int. Cl.
*A61B 18/18* (2006.01)

(52) U.S. Cl. ............................. 606/48; 606/41; 606/45; 606/46

(58) Field of Classification Search ............ 606/41–50, 606/167, 34; 128/898; 604/173–180
See application file for complete search history.

(56) References Cited

U.S. PATENT DOCUMENTS 4,202,337 A    5/1980    Hren et al.

(Continued)

FOREIGN PATENT DOCUMENTS

EP    0 754 437    1/1997

(Continued)

*Primary Examiner*—Roy D. Gibson
(74) *Attorney, Agent, or Firm*—Nixon & Vanderhye P.C.

(57) ABSTRACT

A system and method are disclosed for removing a uterus using a fluid enclosure inserted in the peritoneal cavity of a patient so as to enclose the uterus. The fluid enclosure includes a distal open end surrounded by an adjustable loop, that can be tightened, a first proximal opening for inserting an electrosurgical instrument into the fluid enclosure, and a second proximal opening for inserting an endoscope. The loop is either a resilient band extending around the edge of the distal open end or a drawstring type of arrangement that can be tightened and released. The fluid enclosure is partially inserted into the peritoneal cavity of a patient in a deflated condition and then manipulated within the peritoneal cavity over the body and fundus of the uterus to the level of the uterocervical junction. The loop is tightened around the uterocervical junction, after which the enclosure is inflated using a conductive fluid. The loop forms a pressure seal against the uterocervical junction to contain the conductive fluid used to fill the fluid enclosure. Endoscopically inserted into the fluid enclosure is an electrosurgical instrument that is manipulated to vaporize and morcellate the fundus and body of the uterus. The fundus and body tissue that is vaporized and morcellated is then removed from the fluid enclosure through the shaft of the instrument, which includes a hollow interior that is connected to a suction pump The fundus and body are removed after the uterus has been disconnected from the tissue surrounding uterus.

43 Claims, 16 Drawing Sheets

U.S. PATENT DOCUMENTS

| | | |
|---|---|---|
| 4,381,007 A | 4/1983 | Doss |
| 4,706,667 A | 11/1987 | Roos |
| 5,403,311 A | 4/1995 | Abele et al. |
| 5,411,514 A | 5/1995 | Fucci et al. |
| 5,445,638 A | 8/1995 | Rydell |
| 5,451,223 A | 9/1995 | Ben-Simhon |
| 5,527,331 A | 6/1996 | Kresch et al. |
| 5,735,846 A | 4/1998 | Panescu et al. |
| 5,776,092 A | 7/1998 | Farin et al. |
| 5,776,106 A | 7/1998 | Matyas |
| 5,810,809 A | 9/1998 | Rydell |
| 5,813,409 A | 9/1998 | Leahy et al. |
| 5,814,044 A | 9/1998 | Hooven |
| 5,848,992 A | 12/1998 | Hart et al. |
| 5,882,341 A | 3/1999 | Bousquet |
| 5,904,681 A | 5/1999 | West, Jr. |
| 5,941,876 A | 8/1999 | Nardella et al. |
| 6,102,046 A | 8/2000 | Weinstein et al. |
| 6,224,592 B1 | 5/2001 | Eggers et al. |

FOREIGN PATENT DOCUMENTS

| | | |
|---|---|---|
| GB | 2017302 | 10/1979 |
| GB | 2308980 | 7/1997 |
| WO | WO97/00646 | 1/1997 |
| WO | WO97/00647 | 1/1997 |
| WO | WO9717027 | 5/1997 |
| WO | WO97/24993 | 7/1997 |
| WO | WO97/24994 | 7/1997 |
| WO | WO97/48345 | 12/1997 |
| WO | WO98/27880 | 7/1998 |
| WO | WO99/29250 | 6/1999 |

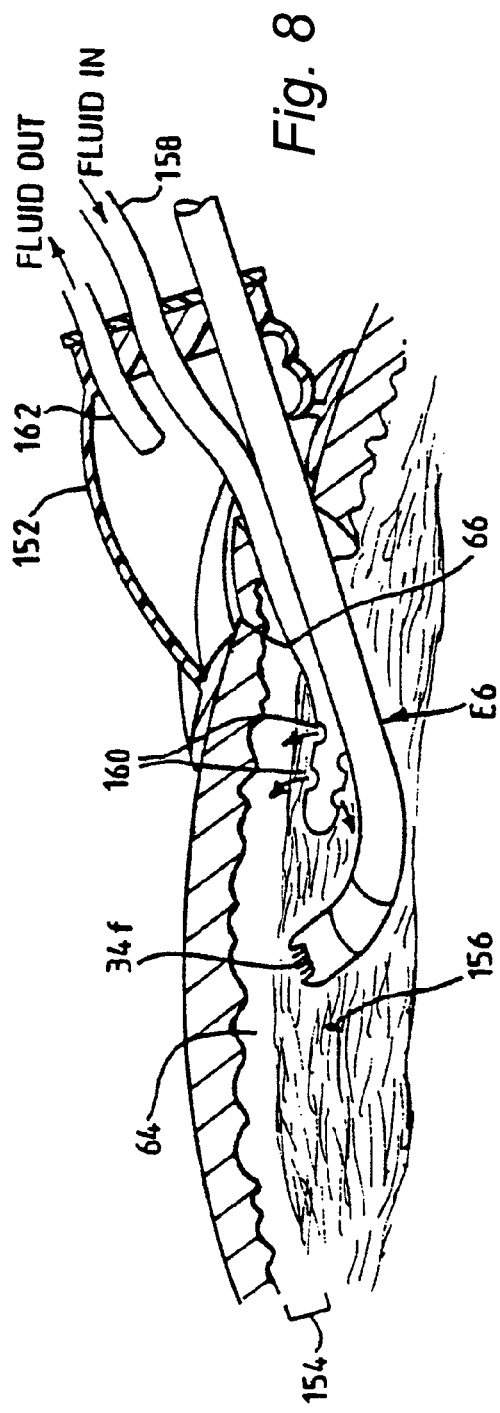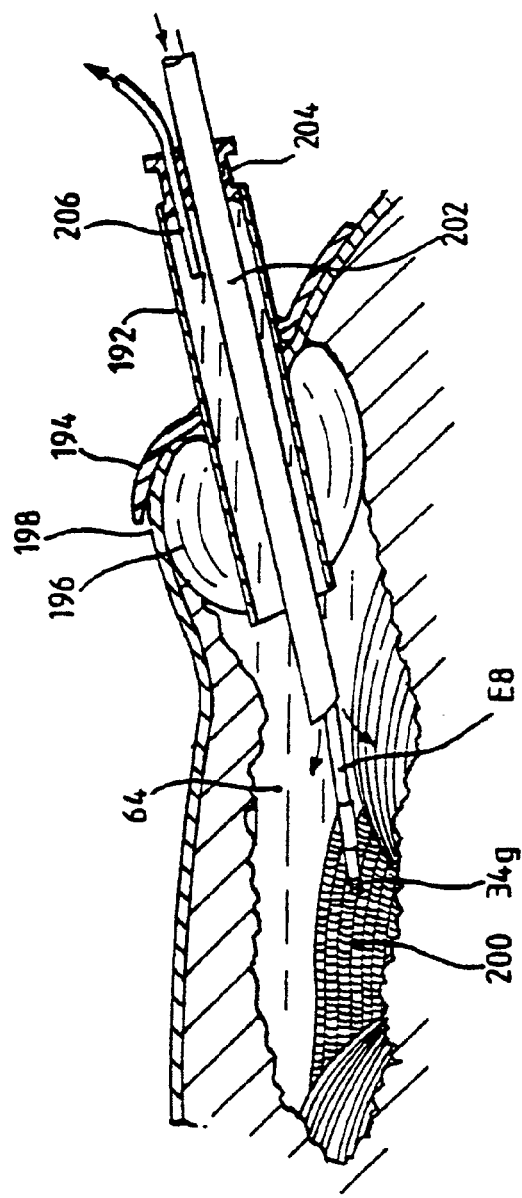

ELECTROSURGICAL INSTRUMENT

CROSS-REFERENCES TO RELATED APPLICATIONS

The present application is a continuation-in-part of application Ser. No. 10/437,431, filed May 14, 2003, now abandoned which is a continuation of application Ser. No. 09/462,927, filed Mar. 27, 2000, now U.S. Pat. No. 6,565,560, which is the national phase of International Application PCT/GB98/02094, filed Jul. 15, 1998, which designated the U.S., and a continuation-in-part of application Ser. No. 10/036,500, filed Jan. 7, 2002, now U.S. Pat. No. 6,923,803 which is a continuation-in-part of application Ser. No. 10/024,348, filed Dec. 21, 2001, now abandoned, which is a continuation-in-part of application Ser. No. 09/484,225, filed Jan. 18, 2000, now U.S. Pat. No. 6,336,926, the entire contents of which are hereby incorporated by reference in this application.

FIELD OF THE INVENTION

The present invention relates to an electrosurgical instrument for the treatment of tissue in the presence of an electrically-conductive fluid medium, to electrosurgical apparatus including such an instrument, and to an electrode unit for use in such an instrument. The present invention also relates to an electrosurgical system for the treatment of tissue in the presence of an electrically-conductive fluid medium, and in particular to such a system including a fluid isolation enclosure for facilitating the immersion of tissues on, or within, a patient's body, such that the system can be operated to vaporise, coagulate, desiccate or otherwise thermally modify such tissues. The present invention further relates to a system and method for removing tissue, such as a uterus, from within a natural body cavity using a fluid enclosure.

BACKGROUND OF THE INVENTION

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical specialty, where one or other of the techniques has particular advantages given the access route to the specific body cavity.

These techniques are selected according to the nature, position and access to the body cavity to be treated. When no such natural body cavity exists, one may be created using a variety of instruments or distensible balloons. This technique is used in such procedures as endoscopic saphenous vein harvesting, endoscopic extraperitoneal hernia repair, and where other subcutaneous tunnels are created to access and perform surgical procedures. Typically, the resulting pouch or cavity is not distended with fluid, and the procedure is conducted with instruments typical of those used to perform laparoscopic surgery (endoscopic surgery performed in the abdominal cavity). Laparoscopic surgery is also performed under gaseous or mechanical distension.

Endoscopes with integral working channels, or those characterised as resectoscopes, are generally employed when the body cavity may be accessed through a natural body opening, such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power leveis have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure direct contact of both electrodes with the tissue.

When either bipolar or monopolar electrosurgery is employed on the skin surface, there is a high risk of excessive thermal damage and tissue carbonisation. This is because the epidermis of the skin has a much higher electrical impedance than more vascular or moist tissues. Such thermal damage and carbonisation can lead to delayed healing, wound infection and excessive scar formation. In addition to these problems, when using bipolar arrangements, the impedance of the electrical contact between the skin and the return electrode can significantly reduce effectiveness. To overcome this problem, prior devices known in the art such as that of U.S. Pat. No. 4,202,337, use multiple arrangements of bipolar pairs in blade or needle-like electrode structures which penetrate the high impedance, superficial layers of the epidermis, such that one or more of the return electrodes makes adequate electrical contact with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrode(s).

The electrical junction between the return electrode and tissue can be supported by wetting of the tissue by a conductive solution such as normal saline. This ensures that the surgical effect is limited to the active electrode, with the electric circuit between the two electrodes being completed by the tissue. One of the obvious limitations with the design is that the active electrode (typically a needle) must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided. Carbon dioxide is the preferred gaseous distension medium, primarily because of its non-toxic nature and high water solubility.

The applicants have developed a bipolar instrument suitable for underwater electrosurgery using a conductive liquid medium. Further details of the instrument and its operation are disclosed in the specification of our European patent application 96918768.1, the contents of which are incorporated herein by way of reference. Operation of this instrument requires that it is immersed in the electrically-conductive fluid, such that the fluid completes an electrical circuit between the two electrodes axially disposed on the shaft of the instrument. The instrument is connected to an electrosurgical generator of the type described in the specification of our European patent application 96304558.8, the contents of which are incorporated herein by way of reference, such that, in operation, the active or tissue treatment electrode of the instrument can produce vaporisation, coagulation, desiccation or thermal modification of tissue structures.

The requirement to immerse the instrument of 96918768.1 limits use to areas of the body which have natural boundaries such that a cavity is formed of dimensions and anatomical position suitable for distension with electrically-conductive liquid, for example in joints, the uterus, the bladder/urethra and the cranial cavity. U.S. Pat. No. 4,381,007 describes the use of a rubber skirt which acts as a damming device for conductive coolant fluid used to bath the cornea of the eye. The purpose of the fluid is to support current flow between two or more electrodes arranged symmetrically and at prescribed distances from the cornea, such that the superficial surface is cooled, whilst tissues deep to the surface are treated sufficiently to correct refractive errors.

The practice of subcutaneous tunneling is also becoming common practice in order to create an artificial cavity in tissues for the purpose of performing endoscopic surgery. Typically, conventional bipolar or monopolar instruments are used, as these artificial cavities are not distended with fluid. These cavities are created between tissue planes using inflatable balloons or expandable blunt instruments through which an endoscope and instruments may be inserted.

The specification of our European patent application 97900315.9, the contents of which are incorporated herein by way of reference, describes an alternative embodiment of the instrument of 96918768.1 and an application of such an instrument to produce thermally-induced shrinkage of the pelvic floor as a corrective treatment of bladder neck descent.

The applicants have also developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment (active) electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of our International Patent Application No. PCT/GB96/01473.

The electrode structure of this instrument, in combination with an electrically-conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangements.

The specification of our International Patent Application No. GB96/01472 describes an irrigated bipolar electrosurgical instrument that can be used in open air or gas-filled environments. This instrument includes an internal channel for feeding electrically-conductive fluid (typically saline) to the exposed end of a tissue treatment electrode so as to provide a conductive fluid path that completes an electrical circuit to a return electrode when the instrument is in use. This instrument also includes an internal channel for removing fluid from the region of the exposed end of the tissue treatment electrode. When the fluid is a liquid, such as saline, the presence of that liquid can cause collateral tissue damage, so its removal is desirable. This type of instrument is intended primarily for use in open air or gas-filled environments, and is not suitable for use with electrosurgical procedures which require distension of a body cavity.

However, where the volume of a body cavity is small—for example in arthroscopic surgery where even the large joints, such as the knee, may only accommodate 50-60 ml of irrigation fluid—the following problems may occur, namely:

(i) Heated fluid in the immediate vicinity of the tissue contact electrode can cause collateral tissue damage;

(ii) The products of the tissue vaporised by the tissue contact electrode can cause visualisation problems; and (iii) Soft tissue present in a joint space tends to move about, making it difficult to apply the active electrode to vaporise such tissue.

An arthroscope electrode may be characterised as short (100 to 140 mm), and rigid with a working diameter up to 5 mm. It can be introduced through a stab incision into a joint cavity (with or without a cannula) using the triangulation technique. Such an electrode is operated with a motion which moves the electrode between the 9 O'Clock and 3 O'Clock positions on the arthroscopic image. As a result, the tissue to be treated is usually approached at a shallow working angle with respect to the axis of the electrode. An arthroscopic electrode thus needs to have an effect consistent with this angled approach to the tissue. The tissue to be treated, such as meniscal cartilage, is commonly dense and of a high electrical impedance. An arthroscope electrode requires output power and voltage settings that reflect the type of tissue being treated, the size of electrode, and the fact that arthroscopists are seeking a speed of effect comparable to that of the mechanical shaver devices they currently employ, albeit with an electrode of smaller dimensions than a shaver blade for improved access.

The specification of our British Patent Application 9612993.7 describes an electrosurgical instrument for the treatment of tissue in the presence of an electrically-conductive fluid medium. The instrument comprises an instrument shaft, and an electrode assembly at one end of the shaft, the electrode assembly comprising a tissue treatment electrode and a return electrode which is electrically insulated from the tissue treatment electrode by means of an insulation member. The tissue treatment electrode has an exposed end for treating tissue, and the return electrode has a fluid contact surface which is spaced from the tissue treatment electrode in such a manner as to define, in use, a conductive fluid path that completes an electrical circuit between the tissue treatment electrode and the return electrode. The electrode assembly is provided with a plurality of apertures in the region of the tissue treatment electrode, through which apertures vapour bubbles and/or particulate material can be aspirated from the region surrounding the tissue treatment electrode.

An RF generator is provided for powering the electrode assembly. The power required from the RF generator to achieve vaporisation depends on a number of variables more fully described in the specification of our International Patent Application No. GB97/00065. Of these variables two, are of particular importance in the context of the present invention: one being the cooling effect produced by the aspiration of conductive fluid in the region of the tissue contact electrode, and the other being the disruption of the vapour pocket formed around the tissue contact electrode by the flow of conductive fluid. These problems can be partially overcome by coordinating the aspiration by monitoring the output features of the generator which indicate the vaporisation power threshold has been exceeded. This usually results in a series of suction pulses as the vaporisation threshold is repeatedly exceeded between pulses and then elevated during the suction pulses so that, should vaporisation be maintained, the suction will be applied continuously. By using this technique, heated saline in the vicinity of the tissue contact electrode and vaporisation products can be successfully removed. The other desirable feature is the aspiration of loose tissue towards the tissue contact electrode, so that it can be stabilised during vaporisation. Whilst this can be achieved according to this technique; there are two significant performance limitations.

The first of these limitations is that the gaseous products of tissue vaporisation contain fatty products which have a sublimation property, i.e., they condense directly to a solid; sublimation occurring at temperatures well above boiling point. As the electrode shaft within the body cavity is cooled by the surrounding saline, these products are easily condensed. Thus, if a parallel suction shaft is used, the build up is along its entire length, and eventually completely blocks the tube. This process, even at the flow rates dictated by minimal influence on the power threshold, can cause very rapid blocking. For example, it is found that, with a moderately large electrode tip, using a 1mm internal diameter suction tube, complete blockage occurs after 30 seconds of activation. Obviously, a larger tube bore would increase the time before blockage, but this occurs so rapidly that the required bore size for a useful electrode life is beyond the dimensions of the maximum shaft diameter. The problems of sublimation are compounded by aspiration of tissue pieces which are incompletely vaporised before being excised from the remainder of the tissue. Given the need to attract tissue and, therefore, the requirement for a strong suction pressure which, once tissue is engaged with the tissue contact electrode and the vaporisation threshold is continually exceeded by cessation of flow, increases the propensity for aspiration of unvaporised tissue and blockage of the aspiration channel.

The second of these limitations also relates to adherence of tissue to the tissue contact electrode. As indicated above, once the tissue obstructs flow, the vaporisation power threshold is exceeded, and suction is continuously applied. Under these circumstances, and particularly when aspiration channels are provided adjacent to the tissue treatment electrode, a steady state can be reached wherein the tissue is held around the periphery of the tissue contact electrode, the portion of tissue in the immediate vicinity of the tissue treatment electrode is vaporised but, without moving the application site or redirecting suction solely through the tissue treatment electrode, no further removal of tissue will occur. For example, large pieces of tissue tend to bridge the tissue treatment electrode, so that all tissue in contact with the electrode is removed, but the bulk of the tissue is left in place. Applying suction solely through the tissue treatment electrode limits the size of the electrode otherwise two extremes are created where, on the one hand during activation in conductive fluid, the vaporisation power threshold is very elevated despite synchronising suction pulses with the RF output, typically >200 Watts, yet, on the other hand, can be reduced to below 50% of this level once tissue is engaged. With a static tissue contact electrode, there is an inevitable compromise between these performances variables.

The aim of the present invention is to provide an improved electrosurgical instrument of this type.

SUMMARY OF THE INVENTION

In a first aspect, the present invention provides an electrosurgical system comprising a radio frequency generator, an electrosurgical instrument, and a fluid enclosure, the generator having a radio frequency output for delivery of power to the electrosurgical instrument when immersed in an electrically-conductive fluid, the electrosurgical instrument having an electrode assembly at the distal end thereof, the electrode assembly comprising a tissue treatment electrode, and a return electrode axially spaced therefrom in such a manner as to define, in use, a conductive fluid path that completes an electrical circuit between the tissue treatment electrode and the return electrode, wherein the fluid enclosure is adapted to surround an operation site on the skin of a patient or an incision leading to a cavity surgically created within the patient's body, wherein the fluid enclosure includes sealing means for sealing against the patient's tissue, and wherein the fluid enclosure includes at least one port through which the electrosurgical instrument is insertable, and through which the electrically-conductive fluid can enter and/or leave the enclosure.

Advantageously, the fluid enclosure is provided with an inlet through which the electrosurgical instrument can be inserted, and preferably the fluid enclosure is provided with port means for supplying electrically-conductive fluid to, and removing said fluid from, the fluid enclosure. The fluid enclosure may be provided with a fluid inflow tube and a fluid outflow tube, each of which is associated with a respective port in the fluid enclosure. Conveniently, the fluid inflow tube is provided with a plurality of apertures at the distal end portion thereof.

Preferably, the inlet is adapted to receive an endoscope, the electrosurgical instrument being insertable, in use, through the endoscope. In this case, the fluid enclosure may be provided with a port through which electrically-conductive fluid can be removed from the enclosure, a working channel within the endoscope constituting a channel for delivering electrically-conductive fluid to the interior of the fluid enclosure.

In a preferred embodiment, the fluid enclosure is provided with a window, through which a surgeon can visualise the region surrounding the tissue treatment electrode. The window may be a magnifying window.

In one preferred arrangement, the electrosurgical instrument is a monopolar instrument having a single, tissue treatment electrode at the distal end thereof, and a metal collar positioned, in use, adjacent to the tissue treatment electrode constitutes the return electrode, the metal collar and the tissue treatment electrode being connected to the generator.

Advantageously, the fluid enclosure is such that it covers an area of skin surrounding the operation site or incision that is substantially larger than the area of the operation site or incision, whereby the volume of electrically-conductive fluid contained in the fluid enclosure is sufficiently large to ensure that its heat capacity is effective to remove heat away from tissue being treated. In a preferred embodiment, the sealing means is constituted by an outwardly-extending flange provided on the fluid enclosure. Preferably, the flange is integrally formed with the fluid enclosure. This fluid enclosure ensures that the electrosurgical instruments of any of the patent applications identified herein can be utilised on the surface of the body or anatomical structure to vaporise, coagulate, desiccate or thermally modify a variety of tissues. Moreover, the fluid enclosure may be used to establish and maintain a fluidic distension of artificial cavities during use of such instruments to vaporise, coagulate, desiccate or thermally modify a variety of tissues. In either case, the fluid enclosure may also include instrument access means to convert standard endoscopic dissection instruments, such that they can be utilised to desiccate or coagulate tissue structures utilising the generator described in the specification of our European patent application 96304558.8.

The invention also provides a fluid enclosure device for use in electrosurgical procedures, the device comprising a translucent flexible web member having a sealing flange at its periphery for forming a substantially fluid-tight seal with a patient's skin thereby to enable tissue to be treated within a substantially fluid-tight enclosure provided by the patient's skin and the flexible web member, and at least a first aperture in the web member to enable introduction of an electrosurgical instrument into the enclosure while maintaining integrity of the substantially fluid-tight seal.

Advantageously, the device further comprises a second aperture to enable supply of electrically-conductive fluid within the enclosure, a third aperture to enable removal of waste matter from within the enclosure, and a fluid outflow tube extending from the third aperture into the enclosure, the outflow tube being buoyant in electrically-conductive liquid.

The invention further provides a method of treating tissue using an electrosurgical system comprising an electrosurgical generator adapted to generate a radio frequency oscillating voltage output across first and second output terminals; an electrosurgical instrument having an active tissue treatment electrode connected to the first generator output terminal; fluid delivery means for delivering electrically-conductive fluid to the tissue to be treated; and a return electrode connected to the second generator output terminal, the method comprising the steps of: enclosing, in a substantially fluid-tight manner, a space within which the tissue to be treated is located, and within which at least the active electrode is located; operating the fluid delivery means at least partly to fill the space with electrically-conductive fluid; operating the generator to apply a radio frequency voltage between the active and return electrodes, and completing at least a part of a conduction path between the active and return electrodes using the electrically-conductive fluid; and manipulating the active electrode in the vicinity of the tissue to be treated.

Advantageously, the method further comprises the step of positioning the return electrode within the space. Preferably, the electrosurgical instrument comprises a shaft, and the active and return electrodes are located on a distal end of the shaft, the method further comprising the steps of positioning the proximal end of the shaft to extend out of the space, and manipulating the active electrode by moving the proximal end of the shaft.

Conveniently, electrically-conductive fluid is supplied to the space continually, and the method further comprises the step of removing waste matter from within the space.

The space may be enclosed by means of a flexible enclosing member which forms a seal with a patient's skin, and the method further comprises the step of reducing the pressure within the space to a level below air pressure in the immediate vicinity outside the space. Alternatively, the space may be enclosed by means of a flexible enclosing member which forms a seal with a patient's skin, and the method further comprises the step of adhesively fixing the flexible member to the patient's skin.

Alternatively, the enclosing step is such that the space encloses a cavity within which the tissue to be treated is situated. The cavity may be a natural body cavity. In this case, the active electrode may be manipulated to achieve at least one of the following: thermal modification of collagen fibres, treatment of parenchyma and mesanchymal tumours. The thermal modification of collagen fibres may be performed to correct bladder neck descent or to treat ligaments or tendons.

One advantage of the invention is that immersion of tissue structures, such as skin, in the electrically-conductive fluid, reduces the impedance of the electrosurgical output, such that skin surfaces can be cut, vaporised, contoured (cutaneous thermabrasion) or otherwise thermally modified, whilst minimising char formation and undesirable thermal damage to tissue margins. This is particularly advantageous when debriding wounds or ulcers, and in the treatment of a variety of cutaneous or dermatological disorders. Such disorders include: malignant tumours (whether primarily or secondarily involving the skin); port wine stains; telangiectasia; granulomas; adenomas; haemangioma; pigmented lesions; nevi; hyperplastic, proliferative and inflammatory fibrous papules; rhinophyma; seborrhoeic keratoses; lymphocytoma; angiofibromata; warts; neurofibromas; condylomata; keloid or hypertrophic scar tissue.

Another advantage of the invention is that the desiccation capability is considerably improved by the immersion of structures in the electrically-conductive fluid, particularly as it applies to simple probe type devices such as hooks. This is a result of several factors. The first of these relates to the fact that tissue surfaces dry out quite quickly during surgical procedures, which increases the impedance of electrical contact with tissues. As desiccation performance is current-driven, the high impedance prevents adequate current delivery, and the output impedance of a desiccate voltage range is exceeded. As a result, the tissue is incompletely desiccated and, if this occurs during desiccation of a blood vessel, the lumen will still be patent and any bleeding will not be controlled. The second of these factors occurs as a result of this high impedance tissue adhering to the surface of the tissue treatment electrode. This compounds the problem, as it further reduces the effectiveness of desiccation. The third is that both these factors are enhanced when the tissue treatment electrode has a small contact surface area, particularly if this electrode is a hook which has been used for cutting, as this leads to carbonisation and pitting of the electrode surface, prior to use as a desiccating instrument. These disadvantages are overcome by use of the present invention. In particular, the improved desiccation performance is useful when sealing venous or thin-walled vascular structures as may be encountered during treatment of haemangioma, varicosities or other vascular anomalies as well as during venous harvesting.

Yet a further advantage of the present invention is that the irrigation of artificial cavities with an electrically-conductive or physiological solution, such as normal saline, provides a number of benefits. The surfaces of tissues exposed during the procedure are prevented from dehydrating, thereby improving their viability, particularly when the healing process is initiated. Tissue debris, electrosurgical smoke and blood are washed from the operative site so improving visualisation. Such devascularised debris produces tissue reactions which could potentially delay healing, increase post-operative pain associated with inflammatory mediators, and increase the risk of wound infection. The consistency of electrical performance of the invention is improved by immersion of the operative site in an electrically-conductive liquid, whereby the voltage potential required to initiate an arc in vapour is more constant compared to the variable effects of different gaseous environments on arc potential.

In another aspect, The present invention also provides an electrosurgical instrument for the treatment of tissue in the presence of an electrically-conductive fluid medium, the instrument comprising an instrument shaft, a tissue treatment electrode mounted at the distal end of the shaft, and removal means, the instrument having an apertured portion through which matter can be aspirated by the removal means from the region surrounding the tissue treatment electrode, the removal means comprising a channel formed within the instrument shaft and leading from the apertured portion, wherein the channel is provided with agitation means movable relative thereto.

The agitation means thus prevents the build-up of sublimation products within the channel.

The instrument may further comprise drive means for moving the tissue treatment electrode relative to the distal end of the shaft.

Advantageously, the instrument further comprises a return electrode which is electrically insulated from the tissue treatment electrode by insulation means, the tissue treatment electrode being exposed at the distal end of the instrument, and the return electrode having a fluid contact surface spaced proximally from the exposed end of the tissue treatment electrodes.

In a preferred embodiment, the tissue treatment electrode is movable cyclically relative to the return electrode so as to move the tissue treatment electrode into, and out of, at least one position in which arcing occurs between the tissue treatment and return electrode.

Preferably, the channel is defined by the instrument shaft, and the agitation means is constituted by a rod mounted within, and movable relative to, the instrument shaft.

Conveniently, the tissue treatment electrode is constituted by the distal end portion of the rod. Thus, movement of the rod results in movement of the tissue treatment electrode, and this prevents tissue bridging, as the tendency for tissue to obstruct the channel is obviated by the electrode movement ensuring that such tissue is treated. Tissue can, therefore, be electrosurgically removed from an operation site by a vaporisation technique, and can be electrosurgically morcellated (that is to say chewed up) in this region by the moving tissue treatment electrode, this process being analogous to a miniature liquidiser.

Advantageously, the rod is constituted by a tungsten wire having a diameter in the range of from 0.2 mm to 1.0 mm. Preferably, the tungsten wire has a diameter in the range of from 0.4 mm to 0.6 mm.

Advantageously, the tissue treatment electrode is angled with respect to the longitudinal axis of the instrument shaft, and the instrument further comprises an insulating sleeve surrounding the rod proximally of said angled end portion. The insulating sleeve may be a ceramic sleeve.

Preferably, the instrument further comprises an insulation member provided at the distal end of the instrument shaft, the insulation member defining said apertured region. The insulation member may be made of a ceramic material.

Advantageously, the insulation member is formed with a slot which constitutes the apertured region. the tissue treatment electrode passing through the slot. Alternatively, the apertured region is constituted by a gap between the tissue treatment electrode and the insulation member.

In a preferred embodiment, the drive means is such as to reciprocate the rod within the channel. Advantageously, the drive means is constituted by a motor and coupling means for converting the rotary output of the motor into reciprocatory movement of the rod.

In this case, the angled end portion of the rod may be at right-angles to the longitudinal axis of the instrument shaft, and the tip of the angled end portion may constitute the tissue contacting portion of the tissue treatment electrode. This electrode is, therefore, a side effect electrode.

In another preferred embodiment, the drive means is such as to rotate the rod within the channel. An electric motor may constitute the drive means.

In this case, the drive rod may be formed with a portion off-set from the longitudinal axis of the instrument shaft.

Advantageously, the angled end portion of the rod is at right-angles to the longitudinal axis of the instrument shaft, and the distal end surface of said angled end portion constitutes the tissue contacting portion of the tissue treatment electrode. The rotation of the angled end portion of the rod permits the use of a small diameter rod, and hence the use of a small tissue treatment electrode, whilst providing a relatively large area tissue contacting position. The use of a small diameter tissue treatment electrode also permits the use of lower electrosurgical powers and/or higher fluid medium flow rates.

Alternatively, the angled end portion of the rod makes an acute angle with the longitudinal axis of the instrument shaft, and the insulation member is provided with an inclined cam surface which is engagable with the apex of the angled end portion of the rod.

It is also possible for the angled end portion of the rod to be bent back around the distal end portion of the insulating sleeve.

Preferably, the removal means further comprises a pump connected to the channel at a region thereof remote from the apertured portion of the instrument. The pump may be activated cyclically whereby matter is aspirated by the removal means in a pulsed fashion. Conveniently, the pump is activated only when the tissue treatment electrode is powered for tissue vaporisation.

The instrument may further comprise an RF generator having a bipolar output connected to the tissue treatment electrode and the return electrode. Advantageously, the RF generator supplies energy to the drive means. Preferably, the pump is controlled in dependence upon the output characteristics of the RF generator.

The electrosurgical instrument of the invention is useful for dissection, resection, vaporisation, desiccation and coagulation of tissue, as well as for combinations of these functions. It has a particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of a disc prolapse or as part of a spinal fusion via a posterior or anterior approach to the cervical, thoracic and lumbar spine or any other fibrous joint for similar purposes; excision of diseased tissue; and haemostasis.

The instrument of the invention is also useful for dissection, resection, vaporisation, desiccation and coagulation of tissue, as well as combinations of these functions, with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURF) including, but not limited to, interstitial ablation of the prostate gland by a percutaneous or perurethral route whether performed for benign or malignant disease; transurethral or percutaneous resection of urinary tract tumours as they may arise as primary or secondary neoplasms, and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele; shrinkage of bladder diverticular cystoplasty procedures as they pertain to corrections of voiding dysfunction; thermally induced shrinkage of the pelvic floor as a corrective treatment for bladder neck descent; excision of diseased tissue; and haemostasis.

The electrosurgical instrument of the invention is also useful for dissection, resection, vaporisation, desiccation and coagulation of tissue and combinations of these functions with particular application in laparascopic, colposcopic (including vaginal speculum) and open surgical procedures on the female genital tract and adnexal related diseases. Laparascopic operative procedures may include: removal of subserosal and pedunculated fibroids, ablation of ectopic endometrium, ovarian cystectomy and ovarian drilling procedures; oophorectomy, salpingo-oophorectomy, subtotal hysterectomy and laparaoscopically assisted vaginal hysterectomy (LAVH) as may be performed for benign or malignant diseases; laparoscopic uterosacral nerve ablation (LUNA); fallopian tube surgery as correction of ectopic pregnancy or complications arising from acquired obstructions; division of abdominal adhesions; and haemostasis.

The electrosurgical instrument of the invention is also useful in the lower female genital tract, including treatment of cervix, vagina and external genitalia whether accessed directly or using instrumentation comprising generally speculae and colposcopes. Such applications include: vaginal hysterectomy and other pelvic procedures utilising vaginal access; LLETZ/LEEP procedure (large loop excision of the transformation zone) or excision of the transformation zone of the endocervix; removal of cystic or septic lesions; ablation of genital or venereal warts; excision of benign and malignant lesions; cosmetic and surgical repairs including vaginal prolapse; excision of diseased tissue; and haemostasis.

The electrosurgical instrument of the invention is also useful for dissection, resection. vaporisation, desiccation and coagulation of tissue and combinations of these functions with particular application in surgery on the ear, nose and throat (ENT), and more particularly procedures performed on the oropharynx, nasopharynx and sinuses. These procedures may be performed through the mouth or nose using speculae or gags or using endoscopic techniques such as functional endoscopic sinus surgery (FESS). Functional endoscopic sinus procedures may include: removal of chronically-diseased inflamed and hypertrophic mucus linings, polyps and neoplasms from the various anatomical sinuses of the skull; excision of diseased tissue; and haemostasis. Procedures on the nasopharynx may include: removal of chronically-diseased inflamed and hypertrophic mucus linings, polyps and neoplasms from the turbinates and nasal passages; submucous resection of the nasal septum; excision of diseased tissue; and haemostasis. Procedures on the oropharynx may include: removal of chronically-diseased, inflamed and hvpertrophic tissue, polyps and neoplasms particularly as they occur related to the tonsil, adenoid, epi-glottic and supra-glottic regions, and salivary glands; as an alternative method to perform the procedure commonly known as laser assisted uvolopalatoplasty (LAUP); excision of diseased tissue; and haemostasis.

It is evident from the scope of applications of the invention that it has further additional applications for dissection, resection, vaporisation, desiccation and coagulation of tissue and combinations of these functions in general laparoscopic, thoracscopic and neurosurgical procedures, being particularly useful in the removal of diseased tissue and neoplastic disease whether benign or malignant.

Surgical procedures using the electrosurgical instrument of the invention may also include introducing the electrode assembly to the surgical site, whether through an artificial conduit (a cannula) or a natural conduit, which may be in an anatomical body cavity or space, or one created surgically. The cavity or space may be distended during the procedure using a fluid, or may be naturally held open by anatomical structures. The surgical site may be bathed in a continuous flow of conductive fluid such as saline solution either to fill and distend the cavity, or to create a locally-irrigated environment around the tip of the electrode assembly in a gas filled cavity. The irrigating fluid may be aspirated from the surgical site to remove products created by application of the RF energy, tissue debris or blood. The procedures may include simultaneous viewing of the site via an endoscope, or using an indirect visualisation means. An irrigated bipolar electrosurgical instrument is described in the specification of our International Patent Application No. PCT/GB96/01472.

The present invention also encompasses a system and method for removing a uterus using a fluid enclosure inserted in the peritoneal cavity of a patient so as to enclose the uterus. The fluid enclosure includes a distal open end surrounded by an adjustable loop, that can be tightened, a first proximal opening for inserting an electrosurgical instrument into the fluid enclosure, and a second proximal opening for inserting an endoscope. The loop is either a resilient band extending around the edge of the distal open end or a drawstring type of arrangement that can be tightened and released. According to the system and method, the fluid enclosure is partially inserted into the peritoneal cavity of a patient in a deflated condition and then manipulated within the peritoneal cavity over the body and fundus of the uterus to the level of the uterocervical junction. The loop is tightened around the uterocervical junction, after which the enclosure is inflated using a conductive fluid. The loop forms a pressure seal against the uterocervical junction to contain the conductive fluid used to fill the fluid enclosure. Endoscopically inserted into the fluid enclosure is an electrosurgical instrument that is manipulated to vaporize and morcellate the fundus and body of the uterus. The fundus and body tissue that is vaporized and morcellated is then removed from the fluid enclosure through the shaft of the instrument, which includes a hollow interior that is connected to a suction pump The fundus and body are removed after the uterus has been disconnected from the tissue surrounding uterus.

BRIEF DESCRIPTION OF THE DRAWINGS

FIGS. 8 and 9 are diagrammatic representations of modified forms of the second embodiment;

FIG. 10 is a diagrammatic representation showing an alternative sealing means for use with any of the forms of the second embodiment;

DESCRIPTION OF PREFERRED EMBODIMENTS

Figure 1:
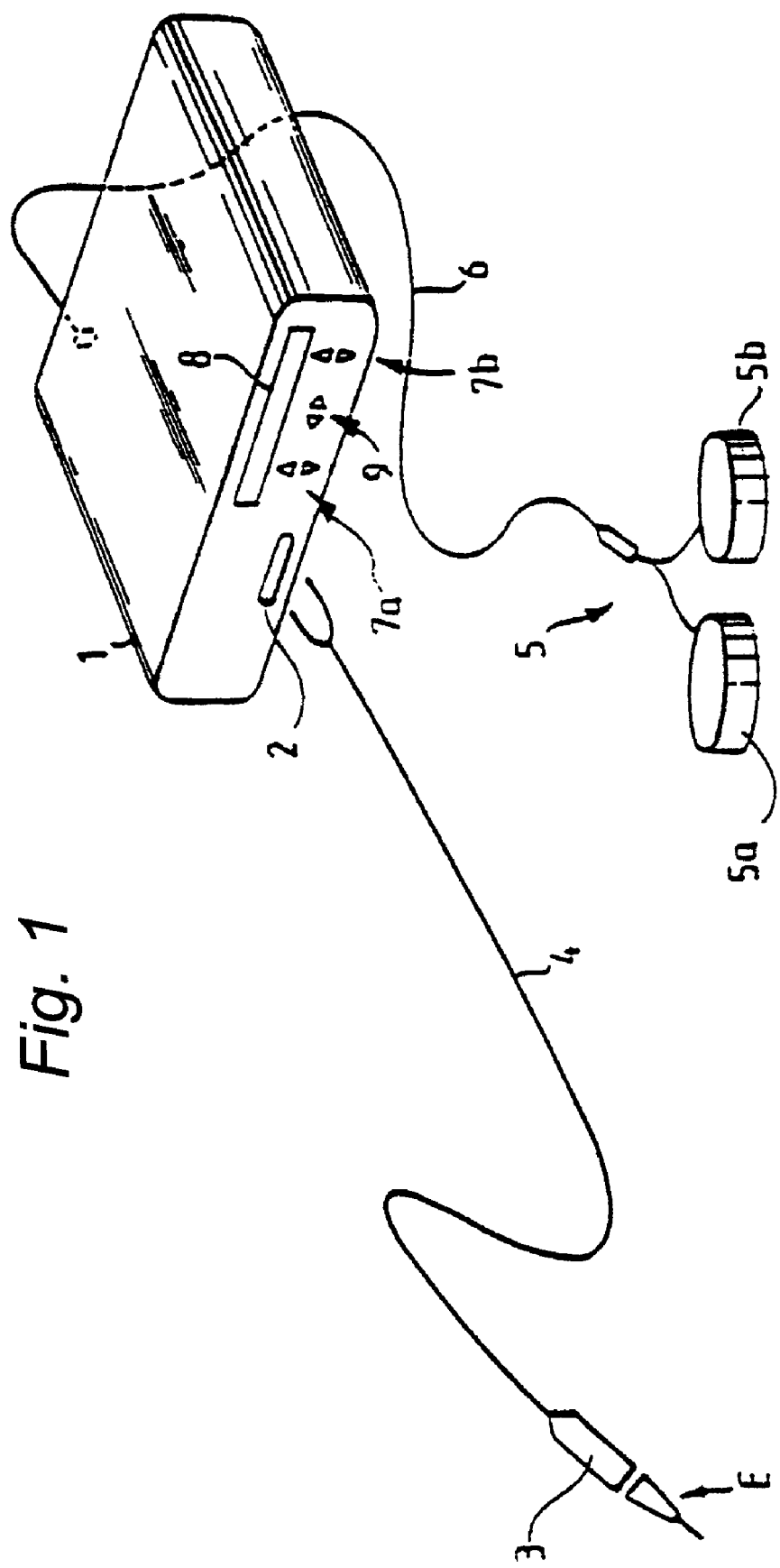
FIG. 1 is a diagram showing an electrosurgical apparatus forming part of the electrosurgical system of the invention.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator I may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footawitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes. The electrosurgical apparatus forms part of an electrosurgical system which can be used for vaporising, cutting, contouring, desiccating, coagulating or otherwise thermally modifying tissue structures on the surface of or close to, the surface of a patient's body. The generator I is described in greater detail in the specification of our European patent application 96304558.8.

The handpiece 3 mounts a detachable electrode unit E, such as the electrode units E1 and E13 to be described below. Other electrode units that can be used with the invention are described in the specifications of our European patent application 96918768.1, British patent application 9600352.0, European patent application 97900315.9, European patent application 97926141.9, European patent application 96918767.3 and European patent application 97900314.2, the contents of which are incorporated herein by way of reference. Alternatively, the electrosurgical instrument may include, instead of the handpiece 3, a connector in the form of a one-piece electrode assembly.

Figure 2:
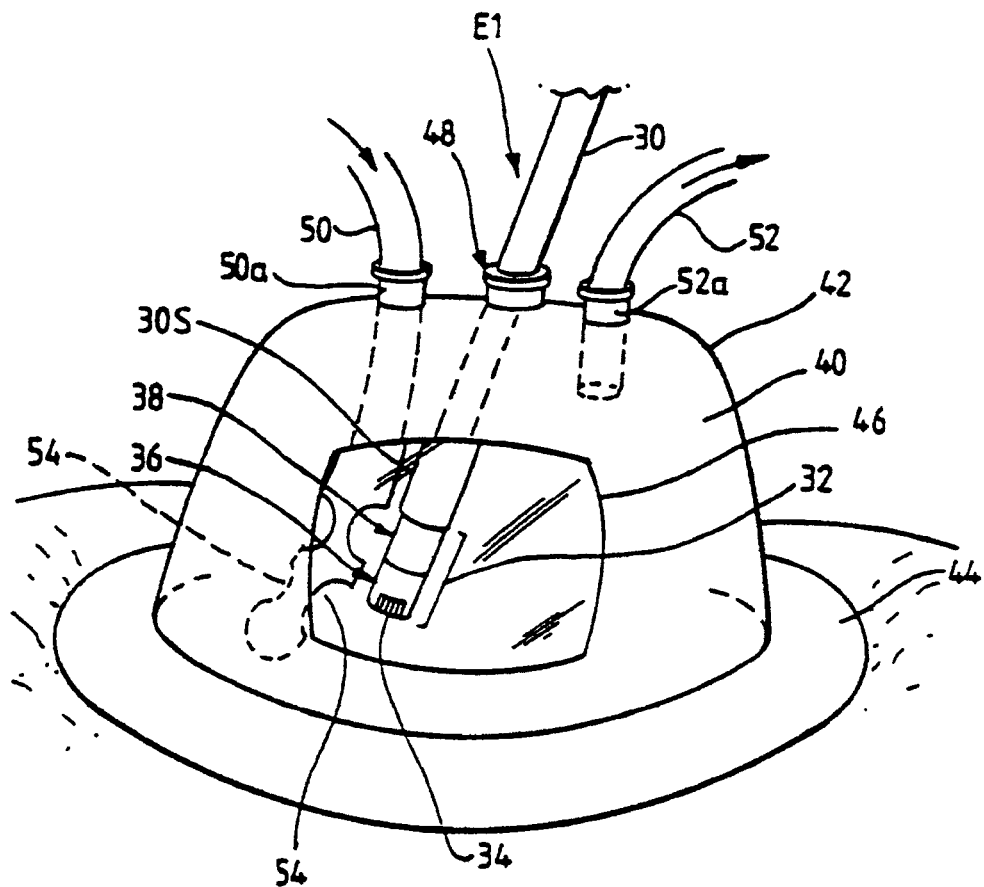
FIG. 2 is a diagrammatic representation, on a larger scale, of a fluid isolation enclosure and an electrode unit of a first embodiment.

In a first embodiment, shown in FIG. 2, an electrode unit E1 is detachably fastened to the handpiece 3 (not shown). The electrode unit E1 comprises a shaft 30 which may be a conductive (e.g., metallic) tube covered with an insulating sheath 30S, with an electrode assembly 32 at the distal end of the shaft. At the other end of the shaft 30 (not shown), means are provided for connecting the unit E1 to the handpiece 3 both mechanically and electrically.

The electrode assembly 32 is bipolar, having an active (tissue treatment electrode) 34 which is axially spaced from a return electrode 38 by means of an insulator 36. The return electrode 38 is constituted by the distal end portion of the tube 30, the portion not being covered by insulating sheet material. In use, the active electrode 32 is positioned in contact with, or in close proximity to, the tissue to be treated. This means that, in normal use when the electrode assembly 32 is immersed in a conductive fluid medium 40, the return electrode 38 remains spaced from the tissue being treated by the insulator 36, and a current path exists between the two electrodes through the conductive fluid contained within an enclosure 42.

To facilitate use of the electrode assembly 32 on the surface of a patient's body, the fluid enclosure 42 is affixed to the surface of the body, to provide a fluid seal, by means of adhesive fixing and sealing means constituted by a flange 44 as shown in FIG. 2. The enclosure 42 is formed with a magnifying window 46 provided in a side wall. The electrode unit E1 can be introduced into the fluid 40 through a port 48 provided in the enclosure 42. More than one port 48 may be provided for simultaneous use of more than one instrument, or for use of an instrument/endoscope combination, wherein the technique of triangulation is employed.

The enclosure 42 is provided with a fluid inflow tube 50 for delivering conductive fluid (such as saline) via a standard fluid injection delivery system (not shown), which system commonly includes a fluid bag and a tubing set. Advantageously, the exit from the fluid inflow tube 50 is positioned in close proximity to the tissue surface to be treated, so that tissue debris and/or blood is removed from the operation site. The enclosure 42 is also provided with a fluid outflow tube 52 positioned at the top of the enclosure, such that bubbles of vapour produced during use are preferentially dispelled from the enclosure. To facilitate removal of vapour, the outflow tube 52, is connected to a conventional vacuum pump (not shown). Additionally, the outflow and inflow may be balanced using an integral inflow and outflow pump. The tubes 50 and 52 enter and leave the enclosure 42 via respective ports 50a and 52a.

If the fluid enclosure 42 is a flexible bag, using a vacuum pump will collapse the bag, which is obviously undesirable. If, however, the fluid enclosure 12 is a rigid structure, then a vacuum pump may be desirable, as it will secure the enclosure to the tissue surface. A flexible enclosure would require positive pressure. Restriction of flow would, then, need to occur at the outlet. There will, in any case, be a danger of a siphon effect, which could cause similar problems as the vacuum pump. The siphon effect can be prevented by an air bleed such s a gas-permaeable membrane.

A further advantage is achieved by providing a diffuse delivery of fluid through a number of apertures 54 in the tube 50, rather than using a single delivery orifice. This overcomes the effects of fluid flow which, when directed at the tissue treatment electrode 34, increases the power required to exceed the vaporisation threshold, shown as point C in FIG. 12, the aspects of which are further described below.

Figure 3:
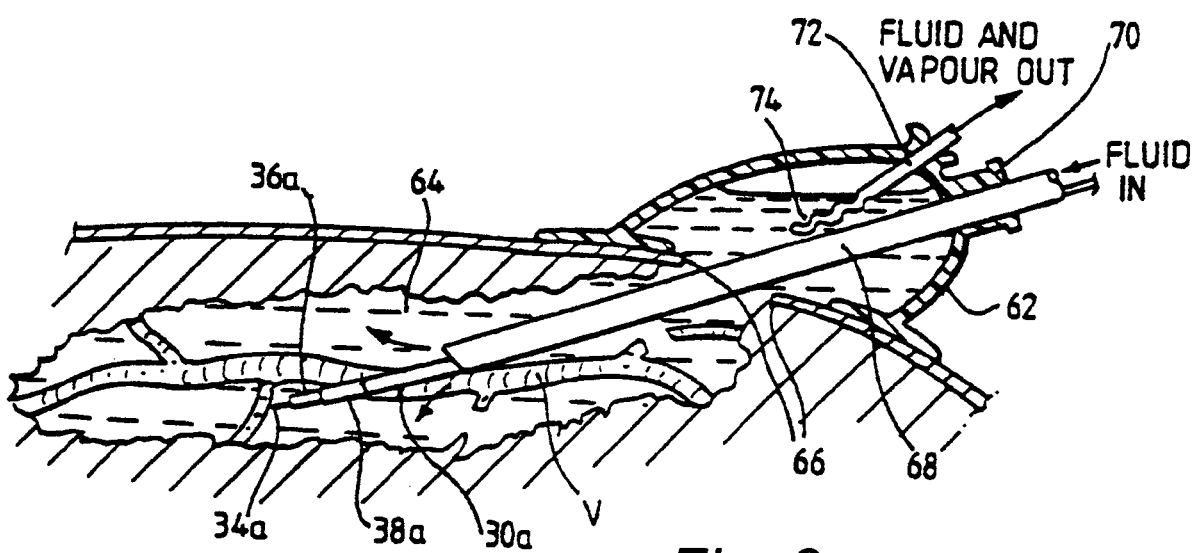
FIG. 3 is a diagrammatic representation of a second embodiment of a fluid isolation enclosure and an electrode unit.

In a second embodiment, shown in FIG. 3, a fluid enclosure 62 is positioned over a site on the patient's body wherein a space 64 has been surgically created in the tissues through an incision 66. This space 64 may be created using a dissecting instrument under endoscopic visualisation prior to application of the fluid enclosure 62, or may be created under a fluid-filled environment using an electrosurgical instrument or instruments based on the electrode assembly 32, or may be based on a combination of the two. Advantageously, the fluid-filled environment, combined with the generator 1 and instrument system for use with the invention, allows the use of tissue treatment electrodes commonly used for dissection, for example, the hook electrode 34a shown in FIG. 3 or a needle electrode. Such electrodes allow the sealing of larger blood vessels than would normally be treated in this way in a gaseous environment. This is particularly beneficial when sealing, for example a large vein such as that shown at V in FIG. 3, during subcutaneous vein harvesting, or as part of the treatment of varicosities.

The electrosurgical instrument of this embodiment is used in conjunction with an endoscope 68 which is inserted through a port 70 in the enclosure 62. In this example, a conductive fluid (such as saline) is introduced through a fluid delivery channel of the endoscope 68. The fluid may alternatively be delivered through a dedicated inflow tube (not shown). In the illustrated example of FIG. 3, the electrosurgical instrument includes an electrode unit E2 including the active electrode 34a, a return electrode 38a constituted by the uncoated distal end of the metallic instrument shaft 30a, and an insulator 36a axially separating the two electrodes. The instrument is inserted through the working channel of the endoscope 68. Alternatively, the instrument my be inserted through a separate port in the enclosure 62, or via a second incision and second enclosure (not shown) positioned to access the same tissue cavity 64. The fluid outflow is provided by holes 74 in an outflow tube 72.

Figure 12:
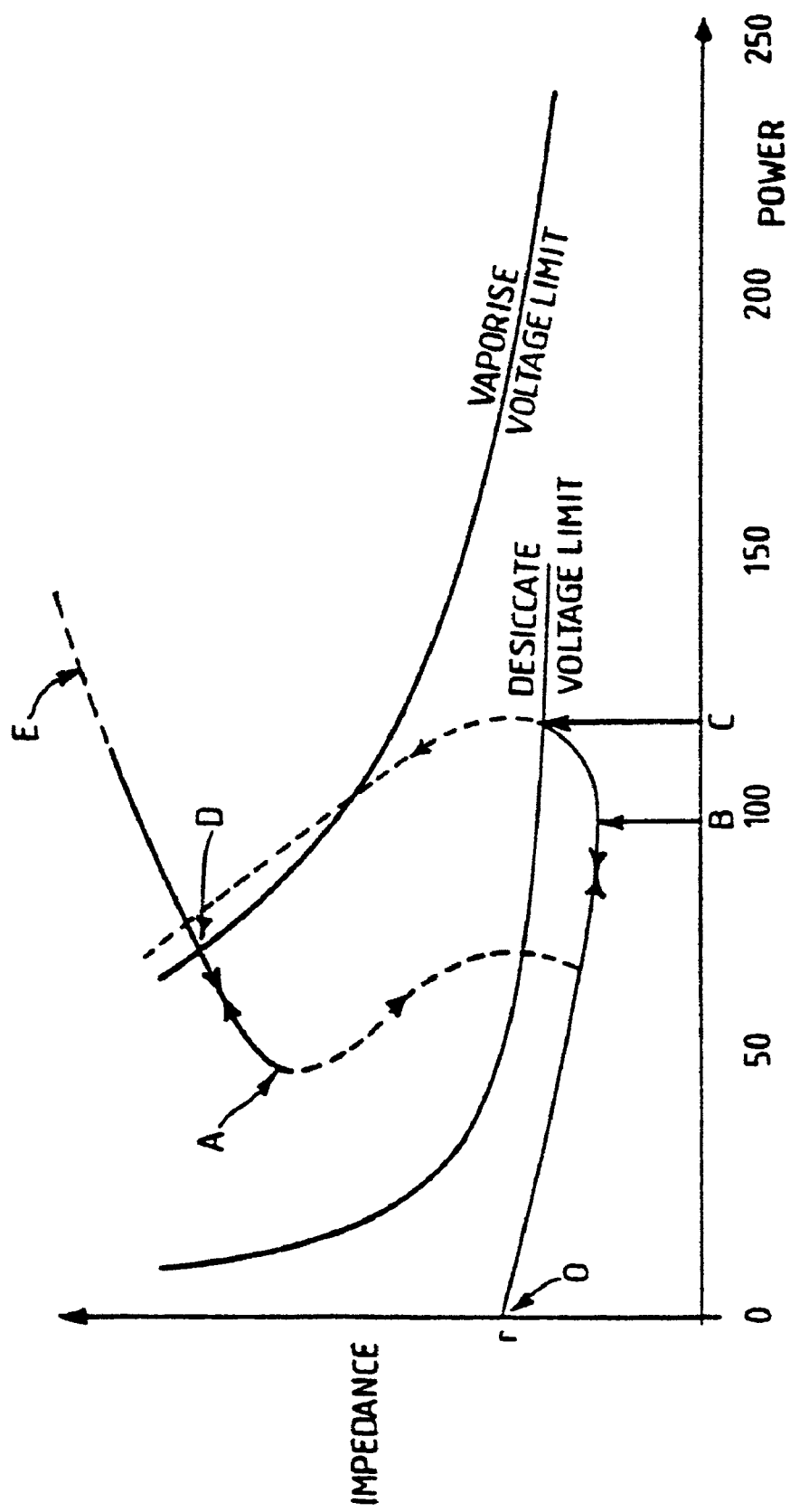
FIG. 12 is a graph illustrating the hysteresis of the electrical load impedance and the dissipated radio frequency (RF) power which occurs during use of a bipolar electrode unit used with the invention in desiccating and vaporising modes.
Figure 13A:
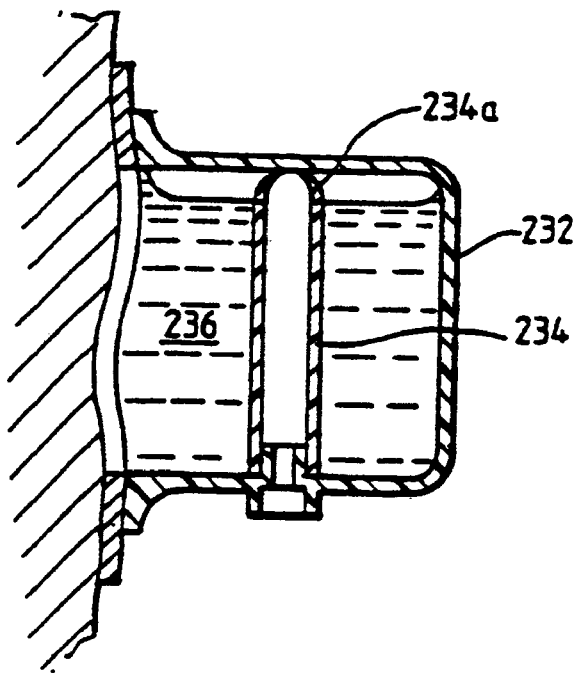
FIGS. 13a to 13d show modified arrangements utilising a fluid outlet tube having a floating tip.
Figure 13B:
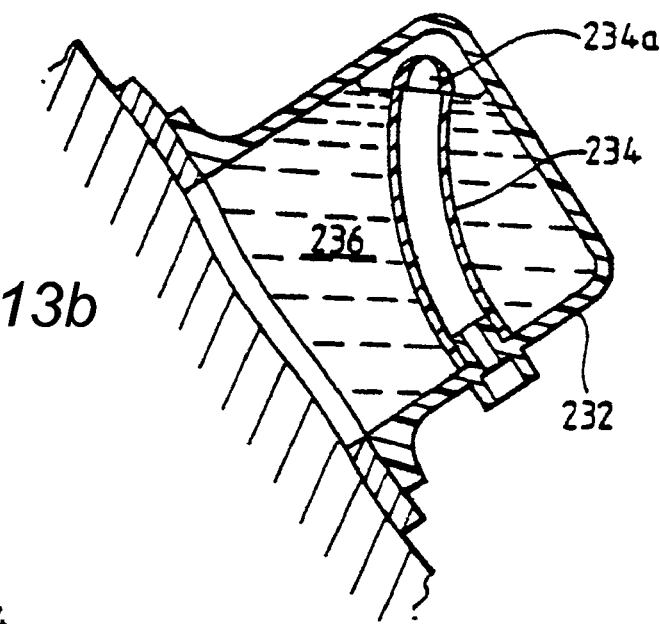
Figure 13C:
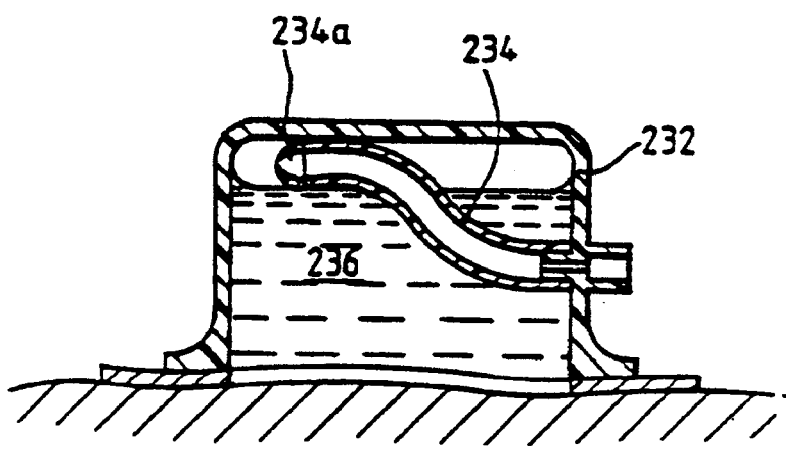
Figure 13D:
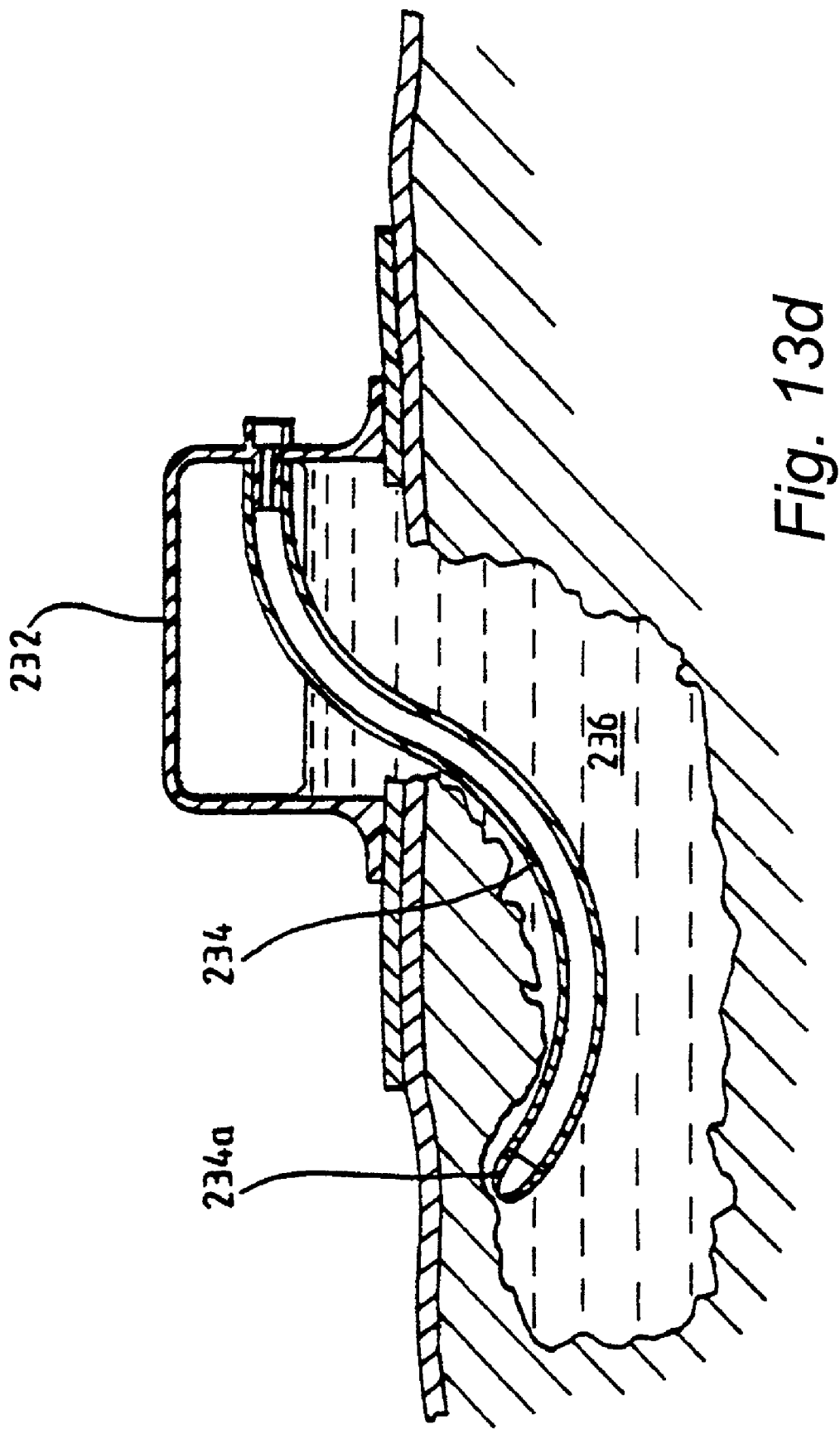

When used in combination with the electrosurgical generator 1 of FIG. 1, the electrode unit E1 of FIG. 2 (or the electrode unit E2 of FIG. 3) can be employed in the conductive fluid medium (saline) for tissue removal by cutting or vaporisation, for sculpturing and contouring menisci for vaporisation, coagulation, desiccation or other thermal modification of tissue on, or within, a patient's body, or for desiccation, depending on the manner in which the generator is controlled. FIG. 12 illustrates how the generator 1 can be controlled to take advantage of the hysteresis which exists between the desiccation and the vaporising modes of the electrode unit E1. Thus, assuming the electrode assembly 32 of the unit E1 is immersed in a conductive medium such as saline, there is an initial load impedance "r" at point "0", the magnitude of which is defined by the geometry of the electrode assembly and the electrical conductivity of the fluid medium. The value of "r" changes when the active electrode 34 or 34a contacts tissue, the higher the value of "r" the greater is the propensity of the electrode assembly 32 to enter the vaporisation mode. When RF power is applied to the electrode assembly 32, the fluid medium heats up. Assuming the fluid medium is normal saline (0.9% w/v), the temperature coefficient of conductivity of the fluid medium is positive, so that the corresponding impedance coefficient is negative. Thus, as power is applied, the impedance initially falls and continues to fall with increasing power dissipation to point "B", at which point the saline in intimate contact with the electrode assembly 32 reaches its boiling point. Small vapour bubbles form on the surface of the active electrode 34 or 34a, and the impedance then starts to rise. After point "B", as power dissipation is increased further, the positive power coefficient of impedance is dominant, so small increases in power now bring about large increases in impedance.

As a vapour pocket forms from the vapour bubbles, there is an increase in the power density at the residual electrode/saline interface. There is, however, an exposed area of the active electrode 34 or 34a not covered by vapour bubbles, and this further stresses the interface, producing more vapour bubbles and thus even higher power density. This is a run-away condition, with an equilibrium point only occurring once the electrode is completely enveloped in vapour. The only means of preventing the run-away condition is to limit applied voltage, thereby preventing power dissipation into higher impedance loads. For given set of variables, there is power threshold before this new equilibrium can be reached (point "C").

The region of the graph between the points "B" and "C", therefore, represents the upper limit of the desiccation mode. The transition from point "C" to the vaporise equilibrium state will follow the power impedance curve for the RF stage of the generator 1 (shown as a dotted line in FIG. 12). Once in the vaporisation equilibrium state, the impedance rapidly increases to around 1000 ohms, with the absolute value depending on the system variables. The vapour pocket is then sustained by discharges across the vapour pocket between the active electrode 34 or 34a and the vapour/saline interface. The majority of power dissipation occurs within this pocket, with consequent heating of the active electrode 34 or 34a. The amount of energy dissipation, and the size of the pocket, depends on the output voltage. If this is too low, the pocket will not be sustained; and, if it is too high, the electrode assembly 32 will be destroyed. It should be noted that, if power were delivered at the same level as point "C", the resulting voltages would cause electrode destruction. The normal operating point for an electrode used for vaporisation is illustrated by point "D". This point is defined uniquely by the combination of the impedance power characteristic for the electrode in conjunction with the vaporise voltage limit. The dotted line E indicates the power level above which electrode destruction is inevitable As the power is reduced, the impedance falls until, at point "A", the vapour pocket collapses an the electrode assembly 32 reverts to the desiccation mode. At this point, power dissipation within the vapour pocket is insufficient to sustain it, so that direct contact between the active electrode 34 or 34a and the saline is re-established, and the impedance falls dramatically. The power density at the active electrode 34 or 34a also falls, so that the temperature of the saline falls below boiling point. The electrode assembly 32 is then in a stable desiccation mode.

Generator power control to achieve the required desiccation, tissue cutting and vaporisation functions is carried out by sensing the peak RF voltage appearing across the output connections of the generator 1, and by rapidly reducing the delivered output power whenever a preselected peak voltage threshold is reached. In a desiccation mode at least, this power reduction is significantly more than that required merely to bring the peak output voltage below the threshold. Preferably the power reduction is at least 50% to take advantage of the hysteresis characteristic described above with reference to FIG. 12.

During use of fluid irrigation, directing the fluid flow to the electrode assembly 32 can cause point "C" (the vaporisation power threshold) to move to the right in the graph of FIG. 12. The power needed to establish a vapour pocket around the active electrode 34 or 34a is, therefore, increased for a given electrode assembly. Hence, it is desirable to disperse fluid flow for a given electrode assembly, either via the fluid inflow tube 50 or the working channel of the endoscope 68.

Figure 4A:
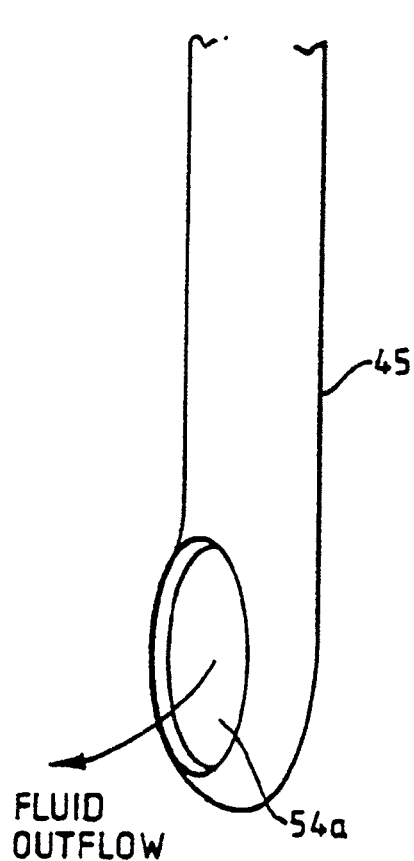
FIGS. 4a to 4d show alternative fluid delivery/evacuation arrangements for use with the first and second embodiments.
Figure 4B:
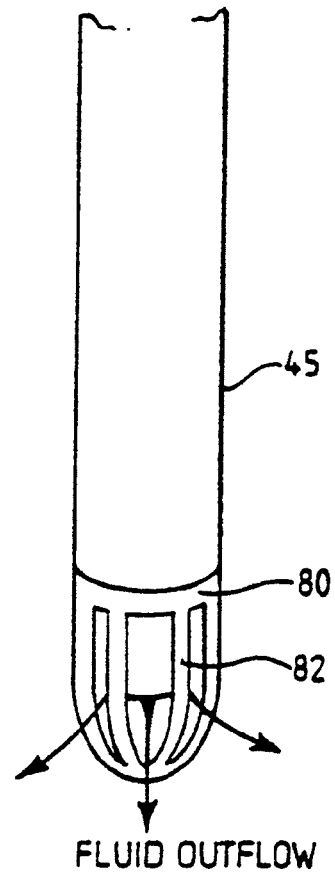

FIGS. 4a to 4d show alternative arrangements for the fluid delivery and outflow tubes. FIGS. 4a and 4b show different terminations for the fluid delivery tube 45 of FIG. 2, these terminations being arranged to dissipate the fluid flow in the vicinity of the operation site, so that the vaporisation power threshold is not significantly increased for a given electrode configuration. In addition to the fluid delivery tube 45 having several inlet apertures 54 as shown in FIG. 2, it could have a single aperture 54a (as shown in FIG. 4a), or it could be a bevelled apertured tube 80 having a distal cage arrangement, the bars 82 of which provide the dispersion of the fluid flow.

Figure 4C:
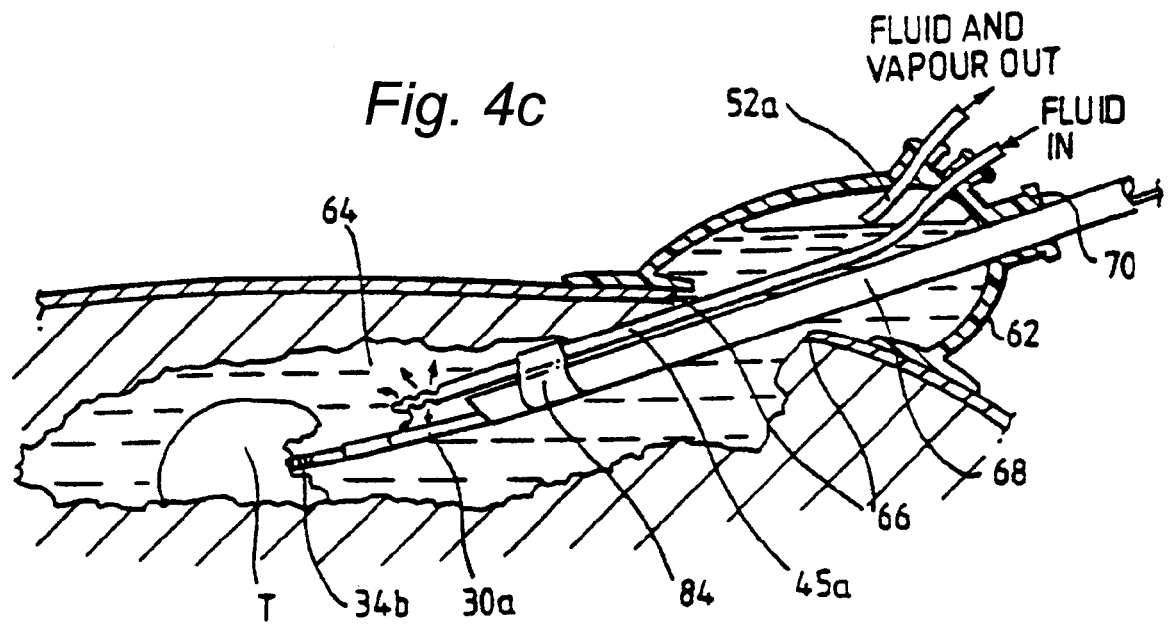

FIG. 4c shows a modification of the arrangement shown in FIG. 3, in which fluid delivery is via a fluid delivery tube 45a, rather than being through the endoscope 68, and fluid and/or vapour is removed via a fluid outflow tube 52a. The fluid delivery tube 45a is extended into the surgically-created cavity 64, and is attached by a clip 84, or similar arrangement, to the endoscope 68. Alternatively, this arrangement could be modified when an endoscope is not needed, in which case the tube 45a could be clipped to any other instrument advanced into the cavity 64. The active electrode 34b shown in this embodiment is constituted by a coil structure which is particularly advantageous in vaporising large fleshy lumps of tissues, such as that shown at T.

Figure 4D:
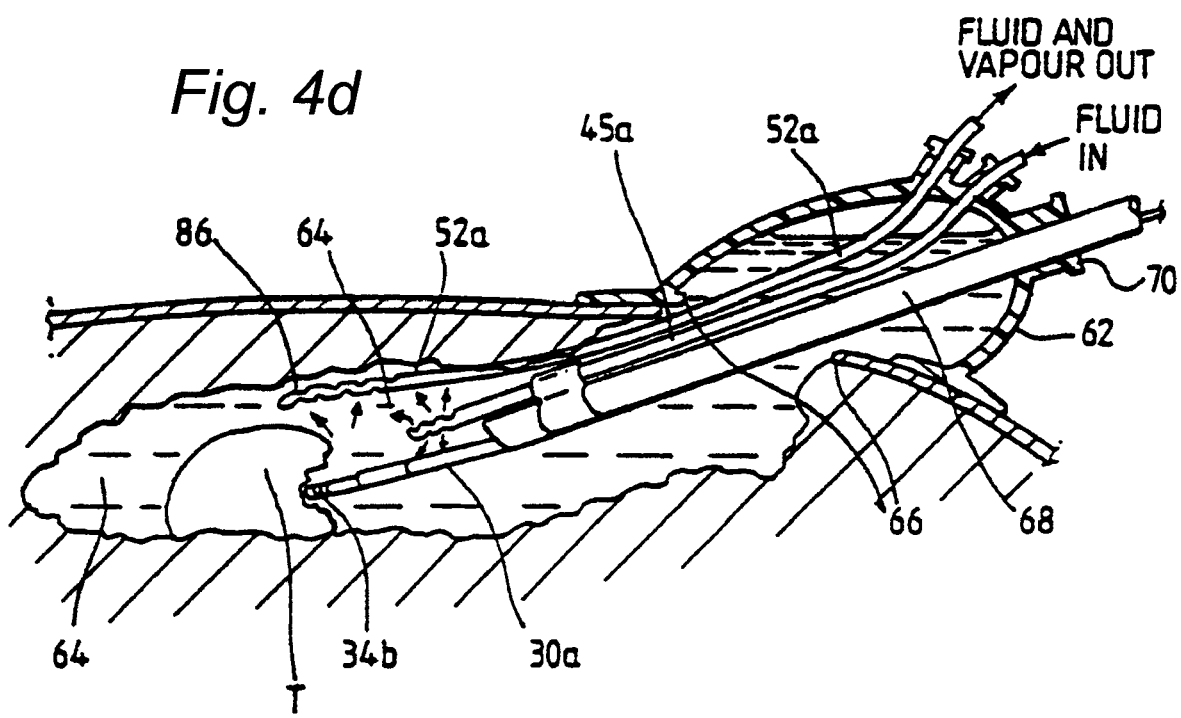

FIG. 4d shows a modification of the arrangement shown in FIG. 4c, in which the fluid outflow tube 52a is extended into the surgically-created cavity 64, such that vapour and fluid can be extracted from the operation site through apertures 86 in the distal end of the outflow tube. This arrangement is particularly advantageous when working in a horizontal orientation, or when the distal end of the cavity is uppermost, thereby avoiding accumulation of vapour in the cavity.

Figure 5:
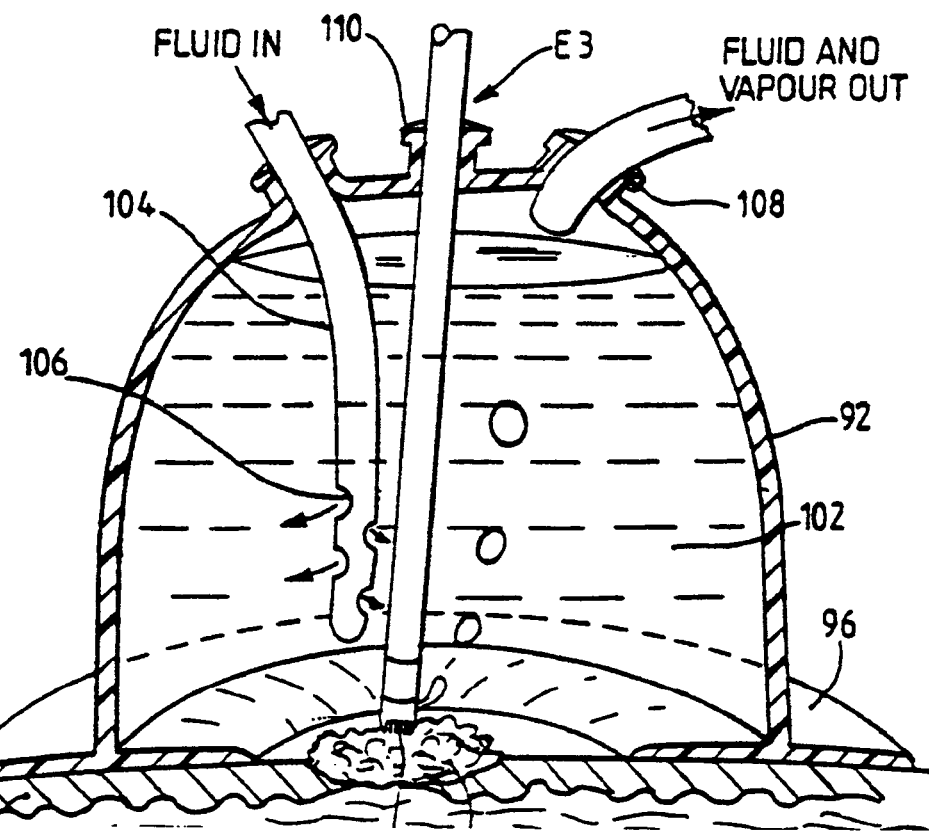
FIGS. 5 to 7 are diagrammatic representations of modified forms of the first embodiment.
Figure 6:
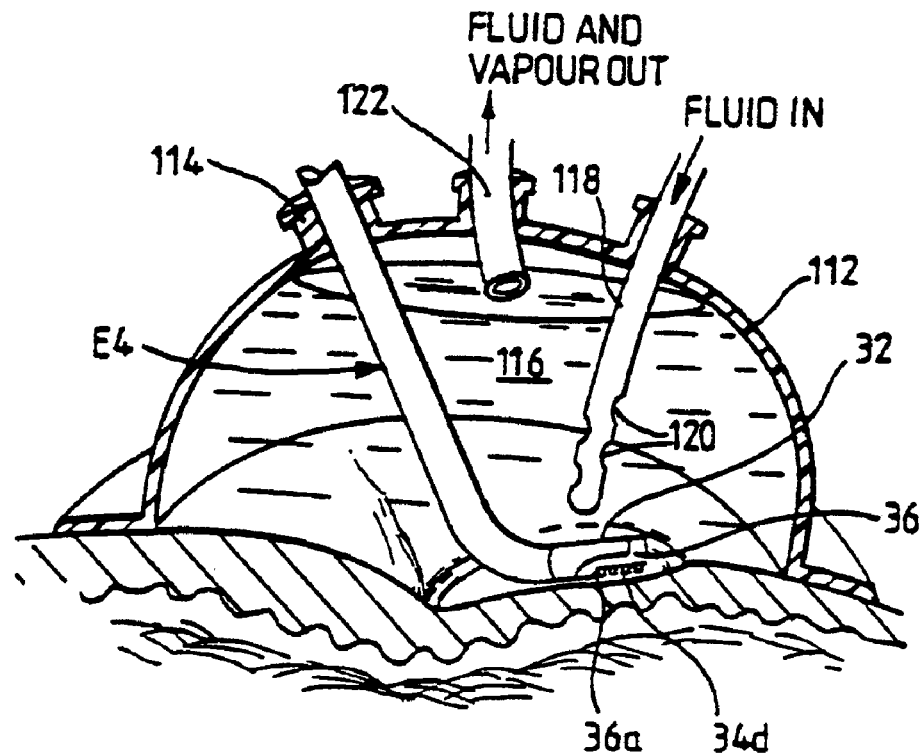
Figure 7:
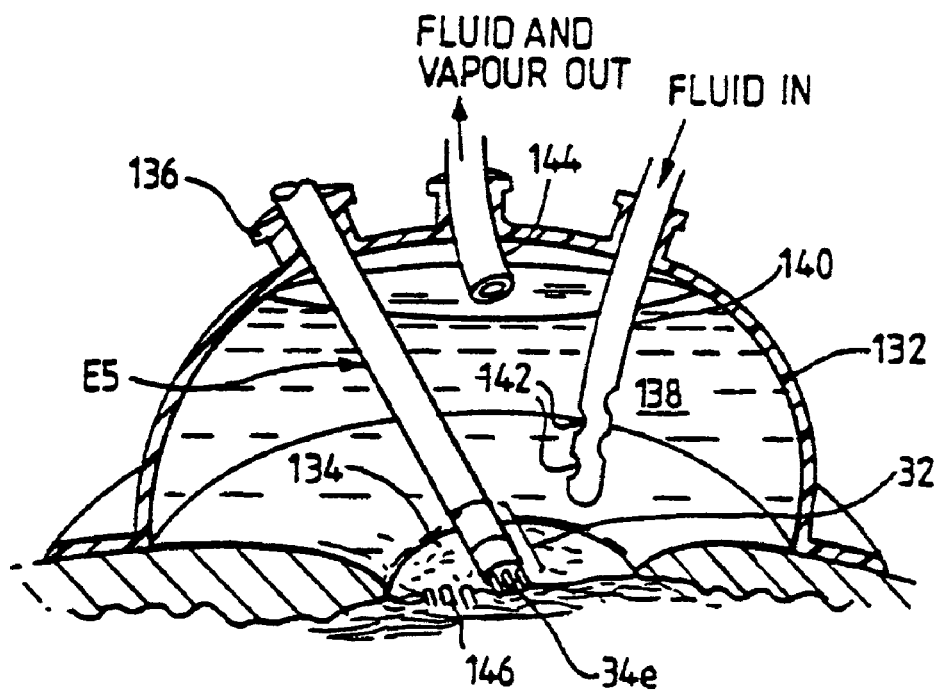

FIGS. 5 to 7 show specific examples of surgical procedures that can be performed with the embodiment of FIG. 2. FIG. 5 shows a cross-section of a modified form of fluid enclosure 92 sealed to the epidermis 94 by a flange 96 formed integrally with the enclosure. The enclosure 92 surrounds a tumour 98 formed in the epidermis 94 above the dermis 100. The tumour 98 is completely immersed in a conductive fluid such as saline 102 which is supplied to the interior of the enclosure 92 via a fluid delivery tube 104, the fluid delivery tube having a plurality of apertures 106 at its distal end. A fluid outflow tube 108 is provided into the top of the enclosure 92 for removal of fluid and/or vapour. An electrosurgical instrument E3 is insertable into the enclosure via a port 110 in the enclosure 92. The electrosurgical instrument E3 is provided with an active electrode 34c in the form of a transverse coil structure. In use, the tumour 98 is progressively removed via vaporisation using the active electrode 34c.

The arrangement shown in FIG. 5 could be modified by incorporating an electrosurgical instrument that can be used to facilitate the excision of a piece of the tumour 98 for hystological examination.

FIG. 6 shows a fluid enclosure 112 which surrounds the surface of skin which is to be contoured during the treatment of superficial skin lesions or for wrinkle removal using the technique of dermabrasion. Here, an electrosurgical instrument E4 is introduced into the enclosure 112 via a port 114. The distal end portion of the instrument E4 is bent substantially at right-angles to the axis of the main body of the instrument, and is provided with a bipolar electrode assembly 32 including an active electrode 34d in the form of a transverse coil. A bipolar electrode assembly incorporating such an active electrode is described in greater detail in the specification of our European patent Application 97926141.9. The active electrode 34d is mounted in a cut-out portion 36a of a ceramic insulator 36, so that it faces laterally with respect to the axis of the distal end portion of the instrument E4. Conductive fluid (such as saline) 116 is introduced into the enclosure 112 via a fluid inflow tube 118 having apertures 120 at its distal end portion. Fluid and/or vapour can leave the enclosure 112 via a fluid outflow tube 122.

FIG. 7 shows a fluid enclosure 132 which surrounds the surface of skin in the region of a chronic ulcerative lesion 134 which is to be treated. An electro surgical electrode ES can be inserted into the enclosure 132 via a port 136. A conductive fluid (such as saline) 138 is introduced into the enclosure 132 via a fluid inflow tube 140 having apertures 142 at its distal end. A fluid outflow tube 144 is provided for removing fluid and/or vapour. The electrosurgical instrument ES includes a bipolar electrode assembly 32 having an active electrode 34e constituted by a plurality of needle filaments. As shown, the active electrode 34e can be used to produce a series of puncture lesions or channels 146 in the chronic ulcerated lesion 134. The aim of creating these lesions 146 is to encourage an angineogenesis such that a more vascular bed is created for grafting or for other corrective techniques. Alternative electrode geometries may be employed to debride such ulcererated lesions, and other surgical procedures will be readily apparent to one skilled in the art.

Figure 9:
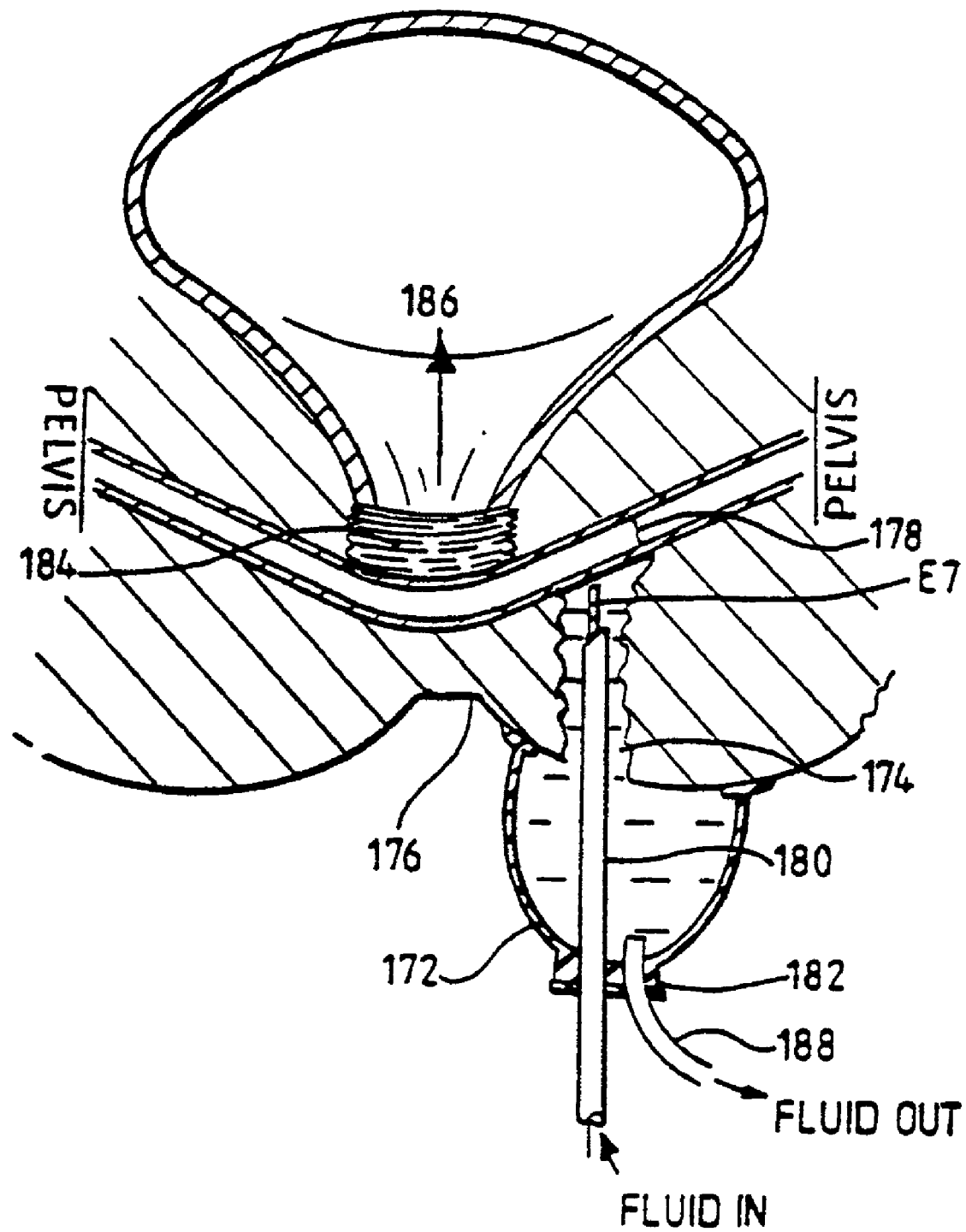

FIGS. 8 and 9 show specific examples of surgical procedures that can be performed with the embodiment of FIG. 3, that is say where a surgically-created cavity 64 surrounds the operation site. FIG. 8 shows a fluid enclosure 152 surrounding an incision 66 leading to the cavity 64. The figure shows the dermal layer 154 of the skin being accessed through a subcutaneous tunnel 156 to facilitate thermal modification of collagen fibres. An electrosurgical instrument E6 is introduced into the tunnel 156 through the fluid enclosure 152, the instrument having a distal end portion which is bent substantially at right-angles to the axis of the main body of the instrument, and being provided with an active electrode 34f in the form of a transverse coil structure. The shaft of the instrument E6 is malleable to allow application of the active electrode 34f to the deep side of the dermis 154. A conductive fluid (such as saline) 158 is introduced through the fluid enclosure 152 to the operation site via a fluid inflow tube 158 having apertures 160 at its distal end. A fluid outflow tube 162 is also provided. The instrument E6 can be used for thermal modification by application of the active electrode 34f by activating the generator 1 (not shown in this figure) in the desiccate mode.

FIG. 9 shows a fluid enclosure 172 which surrounds a surgically-created cavity 174 through the perineum 176 to access the urogenital diaphragm and pelvic floor 178. In this embodiment, an endoscope 180 is used to guide an electrosurgical instrument E7 into the cavity 174. The endoscope 180 is inserted through a port 182 provided in the fluid enclosure 172, with the patient typically being placed in the lithotomy position. The pelvic floor 178, and other collagen containing fascial structures, can be modified (tightened) using the electrode structure of the instrument E7 in combination with the desiccate output from the generator 1 (not shown in FIG. 9) in the treatment of stress urinary incontinence of the female by correction of bladder neck descent. The surgical space can be extended both anteriorly and posteriorly to provide a uniform modification of the structures such that the bladder neck 184 is elevated in the direction 186. Similarly, tendinous structures associated with muscle insertions to bone, joint support structures or ligaments of the body can be treated following repetitive strain injuries, degenerative changes or other injuries, as exemplified by the arrangements shown in FIG. 10. Conductive fluid (such as saline) is supplied to the operation site via the fluid enclosure 172 through the interior channel of the endoscope 180. Fluid leaves the enclosure 172 via a fluid outflow tube 188.

FIG. 10 illustrates a modified form of fluid enclosure 192 constituted by a generally tubular member provided with a sealing flange 194. An inflatable balloon 196 is mounted on the fluid enclosure 192, and can be used to apply pressure between the surface 198 of the skin and the sealing flange 194. A ligamentous structure 200 (such as the lateral ligament of the knee) of the patient's body can be treated by an electrosurgical instrument E8 which is introduced into a surgically-created cavity 64 adjacent thereto via an endoscope 202. Conductive fluid (such as saline), is introduced into the cavity 64 through the working channel of the endoscope 202. An endoscope/instrument and fluid management port 204 is provided, and this may also include fluid delivery channels. Fluid is removed via a fluid outflow tube 206 mounted in the port 204. In use, the balloon 196 is inflated with liquid or gas, once the device is positioned through an incision 208 in the skin 198, using an inflation tube (not shown). Alternatively, the sealing flange 194 may constitute a second balloon for sealing around the aperture to the surgical cavity 64. The electrosurgical instrument E8 includes an active electrode 34 g having a coiled structure.

Figure 11:
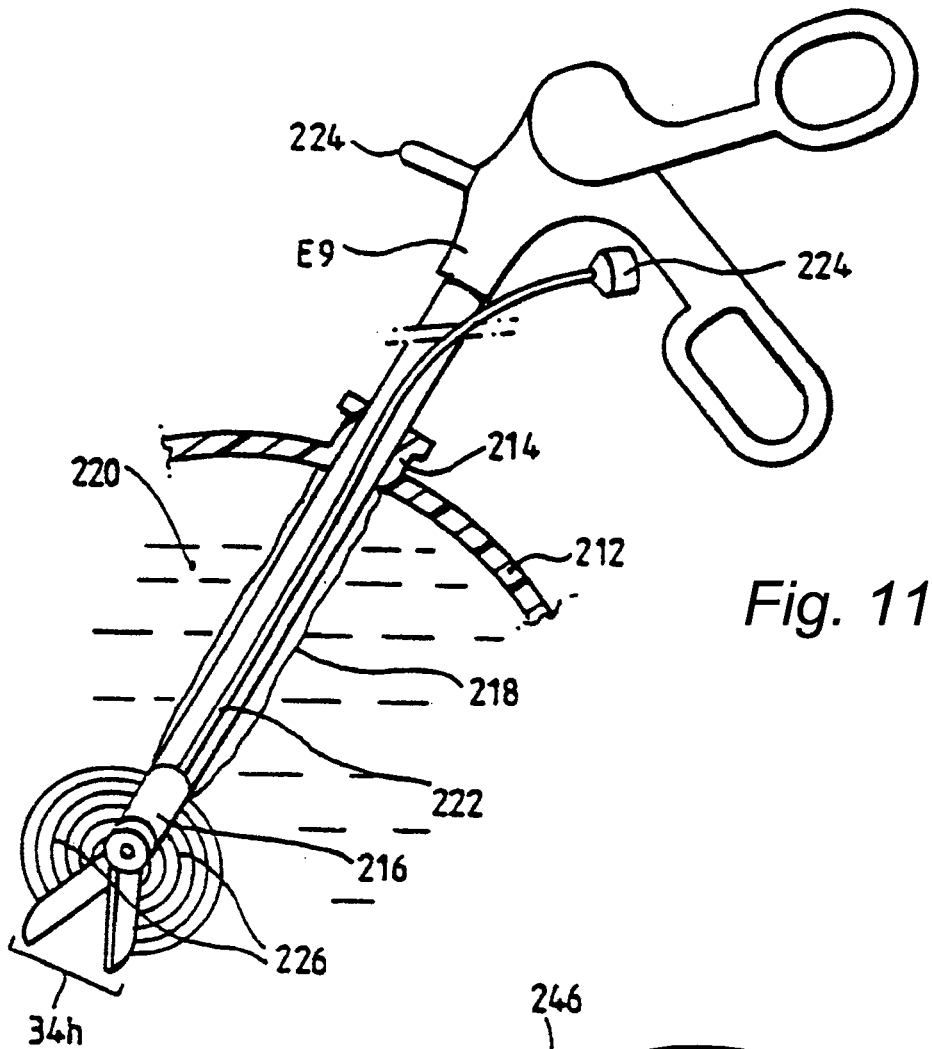
FIG. 11 is a diagrammatic representation of a further modification for use with either the first embodiment or the second embodiment.

FIG. 11 illustrates a means of using the invention with a conventional monopolar electrosurgical instrument, such as that shown at E9. The instrument E9 can be inserted through a port 214 in a fluid enclosure 212. The instrument E9 of this embodiment can be used for surgical procedures on the skin surface or in artificially-created cavities within the patient's body. Accordingly, the enclosure 212 (part only of which is shown in FIG. 11) could be of any of the types previously described. However, even though the instrument E9 is itself a monopolar instrument, it is used in a bipolar configuration by providing a return electrode 216 mounted at the distal end of a thin sleeve 218 which is fixed to the shaft of the instrument so that a fixed relationship is maintained between the return electrode and the active electrode 34h, which here is constituted by a scissors arrangement. Conductive fluid (such as saline) 220 is introduced into the enclosure 212 by a fluid inflow tube (not shown). Similarly, a fluid outflow tube (not shown) is provided for removal of conductive fluid 220. The return electrode 216 is electrically connected by a cord 222 and a connector 224 to one side of the bipolar electrosurgical output of the generator 1 (not shown in this figure). A monopolar connector post 224 of the instrument E9 is connected to the other side of the generator. In use, the generator can be energised in the desiccation mode to create an electric field pattern 226 so that the active electrode 34h can be used for coagulation or desiccation of tissue in a bipolar mode. The vaporising or cutting output of the generator cannot be used in this embodiment.

Another aspect to the invention is the use of a fluid outflow tube with a floating tip, as shown in FIGS. 13a to 13d. In each of these figures, a fluid enclosure 232 includes a fluid outflow tube 234, the tip 234a of which is made of, or incorporates, buoyancy material, so that the tip floats within electrically-conductive fluid (such as saline) 236 within the enclosure, with the tube inlet within the "air space" at the top of the enclosure. In this way the tip floats to areas where gases produced by vaporisation are easily removed.

Figure 14:
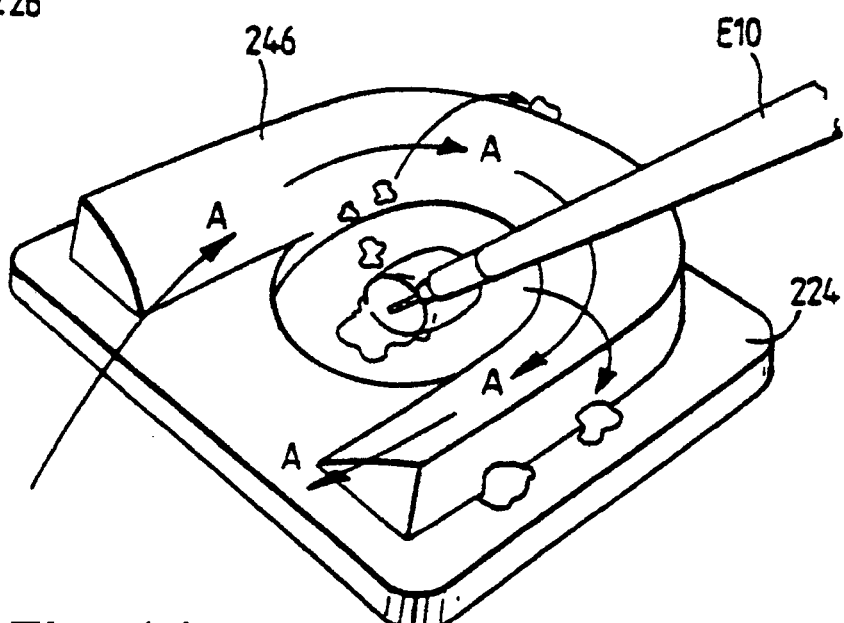
FIG. 14 shows a further modified arrangement.

Another aspect of the invention (shown in FIG. 14) is that, by using a fluid inflow tube (not shown) at a tangent to a fluid enclosure (only the base 244 of which is shown), a rotating fluid current can be generated. This rotating current, indicated by the arrows A, causes tissue debris produced by an electrosurgical instrument E1O to be thrown outwardly away from the central treatment region. The base 244 of the enclosure is constructed in such a way to trap this debris. The enclosure base 244 incorporates a ridge 246 to capture debris and prevent it from returning to the operative site.

In order to facilitate visualisation of an operation site, each of the fluid enclosures 42, 62, 92, 112, 132, 152, 172, 192, 212, and 222 could be made of translucent or transparent material.

Figure 15:
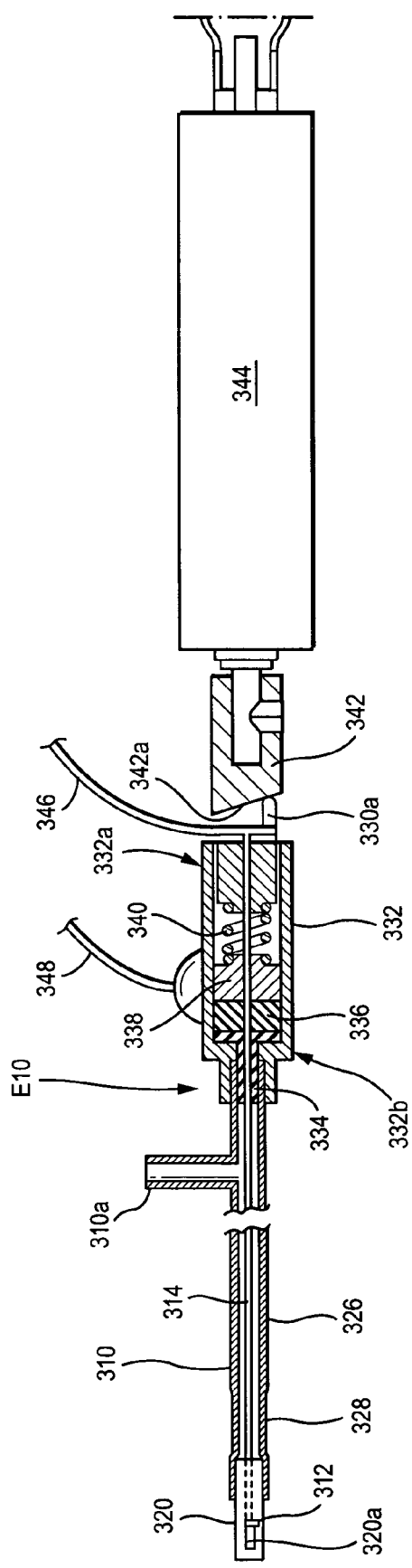
FIG. 15 is a diagrammatic side elevation, partially broken away, of a first form of electrode unit constructed in accordance with the invention.

FIG. 15 shows the first form of electrode unit E10 for detachable fastening to the electrosurgical instrument handpiece 3, the electrode unit comprising a shaft 310, which is constituted by a tube made of stainless steel. A tissue treatment (active) electrode 312 is provided at the distal end portion of the shaft 310. The active electrode 312 is provided by the distal end portion of a rod 314 made of tungsten. the active electrode extending at right angles to the rod. The rod 14 has a diameter of 0.4 to 0.6 mm. A ceramic tube 318 is fixed to the rod 14 immediately adjacent to the active electrode 312. A ceramic tip 320 is fixed within the out-turned distal end portion of the shaft 310.

As shown in FIG. 15, the active electrode 312 protrudes through a longitudinal slot 320a formed in the ceramic tip 320. That portion of the rod 314 not covered by the ceramic tube 318 is provided with an insulating sleeve 322 made of polyimide, polytetrafluoroethylene or by separate sleeves made by these two substances. A heat sleeve 324 made of polytetrafluoroethylene or polyimide, covers the adjoining regions of the ceramic tube 318 and the sleeve 322.

The major portion of the length of the shaft 310 is provided with an insulating heat shrink sleeve 326 made of polyvinylidenefluoride. The sleeve 326 does not cover the distal end portion of the shaft 10, that region of the shaft constituting a return electrode 328.

The rod 314 is mounted for reciprocal movement within the shaft 310, that end of the rod remote from the active electrode 312 being fixed to a coupling member 330 slidably mounted within one end 332a of a sleeve 332 made of stainless steel. The other end 332b of the sleeve 332 is fixed to the adjacent end portion of the shaft 310. A top hat washer 334 is located within the sleeve end 332b, the washer constituting a backing member for a silicone gland 336 and a delrin bush 338. A return spring 340 acts between the bush 338 and the coupling member 330. The rod 314 passes through apertures in the washer 334, the gland 336 and the bush 338.

An off-set shaft 330a is fixed to the end face of the coupling member 330, the free end of this shaft being engageable with an inclined end face 342a of a rotatable coupling member 342 fixed to the rotary output shaft of a motor 344. Hence, rotation of the output shaft of the motor 344 results in reciprocation of the coupling member 330 and the rod 314.

The hollow interior of the shaft 310 is connected to a transverse tubular member 310a which is connected to a suction pump (not shown), and so constitutes a suction/exhaust port. As shown in FIG. 15, the active electrode 312 is positioned at the end of an aspiration channel constituted by the annular cavity defined by the interior of the shaft 310 and the rod 314, so that vapour bubbles and/or particulate material which, in use, are formed in the region of the active electrode, can be aspirated from the region for removal via the slot 320a, the aspiration channel and the port 310a.

The RF generator 1 (not shown in FIG. 15) delivers an electrosurgical current to the electrodes 312 and 328 via connectors 346 and 348 provided respectively on the coupling member 330 and on the sleeve 332. The generator 1 includes means for varying the delivered output power to suit different electrosurgical requirements. Thus, in a first output power range of from about 140 volts to 200 volts, the active electrode 312 is used for tissue desiccation; and, in a second output power range of from about 250 volts to 600 volts, the active electrode is used for tissue removal by cutting or vaporisation. For both ranges, the voltages are peak voltages. The generator 1 may be as described in the specification of our European Patent Application 96304558.8.

This electrosurgical instrument is particularly useful for rapid tissue debulking and the removal of loose tissue. One of the problems which could be encountered when tissue is rapidly debulked using an arthoscopic electrode configuration, particularly when working in small joint spaces. is the production of vapour bubbles generated as an end product of tissue vaporisation. Such bubbles obscure vision, and can coalesce at the site of tissue application, so that an electrical circuit between the active and return electrodes having filamentary, mesh or coiled spring forms goes some way to solving this problem as it reduces the vaporisation threshold as disclosed in the specification of our International patent application No. GB97/00065.

The provision of the suction pump ensures the elimination of vapour bubbles from an operation site, which is particularly advantageous during aggressive tissue debulking. The suction pump is activated only when the active electrode 312 is powered for tissue vaporisation. The pump is, therefore, pulsed so as to pull saline over the active electrode 312 (and to extract vapour bubbles and/or particulate material). This cools the active electrode 312, resulting in the collapse of the vapour pocket surrounding the active electrode. This, in turn, leads to the suction pump being turned off, thereby reducing the flow of saline over the active electrode 312. This electrode 312 then heats up again, leading to the reformation of a vapour pocket, and the re-activation of the suction pump. This cycle then repeats until the generator 1 is turned off when the instrument is removed from the operation site.

The suction pump must be controlled so that the flow of bubbles from the active electrode 312 is balanced to the output characteristics of the RF generator 1 to prevent excessive cooling of the active electrode and a resultant increase in its vaporisation power threshold. The thermal mass of the thin, wire-form active electrode 312 is lower than that of a standard solid form active electrode, and this assists in rapidly re-establishing the vapour pocket around the active electrode should this collapse following excessive cooling.

The electrode unit E10 is intended primarily for use in arthroscopic surgery which requires rapid tissue debulking by vaporisation. The side-effect electrode (i.e. where the treatment axis is perpendicular to the shaft) configuration of the unit E10 is particularly advantageous for this purpose. In use, the electrosurgical instrument is manipulated to introduce the electrode assembly constituted by the active electrode 312 and the return electrode 328 into a selected operation site (e.g. within the joint space of a knee), so that the active electrode contacts the tissue to be treated, and the tissue and the electrode assembly are immersed in saline.

The footswitch 5b (or the push button 7b) is then operated to activate the generator 1. The generator 1 then provides sufficient RF power to the electrode assembly to vaporise the saline surrounding the active electrode 312, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface. With tissue engagement, the flow of irrigant away from the active electrode 312 will be reduced, the amount of reduction depending on the nature of the tissue surface, the application pressure and the suction pressure. Speed of debulking will, therefore, depend on these variables. Once the vaporisation occurs, the products will include vapour bubbles, carbon particles and tissue debris. All of these products are removed from the region of the active electrode 312, via the shaft 310 and the port 310a, by the suction pump.

All the constituents removed from the active tip are at high temperatures. This could lead to a potentially dangerous heating of the electrode shaft 310, which could cause tissue damage at the entry point. It may be, therefore, necessary to aspirate additional coolant saline from the body cavity along the inside surface of the shaft. To ensure that this saline is indeed at a safe temperature, it is taken from the rear of the return electrode 328 via a mesh filter (not shown).

In use, when the generator 1 is turned on, the motor 44 begins to rotate, causing the rod 314 to oscillate with an amplitude of 0.5 mm. The oscillation of the rod 314 within the shaft 310 provides a mechanical agitation within the shaft that is sufficient to dislodge any sublimation products which condense within the shaft. In this way, blockage of the shaft 310 is prevented, so that the instrument can be used on a continuous basis.

The oscillation of the active electrode 312 also ensures that tissue pieces removed electrosurgically by vaporisation from an operation site are morcellated electrosurgically by the oscillating electrode, thereby preventing large tissue pieces bridging the aspiration channel. Morcellation is the division of a tissue piece into many smaller pieces in order to facilitate its surgical removal.

The electrode unit E10 is also very effective in removing heated saline (distension fluid) from within a joint cavity. The risk of hot distension fluid occurs primarily during power application to reach the vaporisation threshold. Once the threshold has been reached, the power requirement falls by 30-50%.

Whilst aspiration from the region of the active electrode 312 will remove heated saline from the body cavity, and remove any risk of overheating through prolonged activation under conditions where the vaporisation threshold is not reached, the cooling effect and disruption of vapour pockets created around the active electrode will increase the vaporisation threshold. A vicious cycle can, therefore, be created, wherein the more suction applied at the active electrode 312, the more power required to reach the vaporisation threshold, and the greater the risk of heating. The other factor influencing the vaporisation threshold is the ratio of return: active contact area, and the insulation separation between the active electrode 312 and the return electrode 328. The size of the active electrode 312 and the insulation separation, must, therefore, be reduced to the minimum necessary to achieve the function in order to offset the effects of aspiration in elevating the power threshold of vaporisation.

The specification of our International Patent Application GB97/00065 discloses techniques for controlling the vaporisation threshold by employing active electrode designs which assist in capturing vapour pockets and preventing cooling of the active electrode application site by screening from the flow of irrigant provided by channels in an endoscope. An alternative method of reducing the vaporisation power threshold is to pulse the suction pressure, thereby allowing the threshold to be attained between pulses. Such pulses may be synchronised with the output features of the RF generator 1 to provide power bursts during active suction to sustain the vapour pocket, and clear any tissue occluding the apertures in the active electrode 312.

A known technique in arthroscopic surgery is to apply suction through a mechanical, tissue-nibbling device so that soft tissue present in the joint space, such as the infrapatellar fat pad, can be held in position within the nibbler jaws by suction whilst it is progressively "nibbled away".

Attracting tissue to the active electrode 312 of the electrode unit E10 has a similar effect as, for the reasons already given above, compliant tissue adhering to the active electrode will result in a reduction of the vaporisation power threshold. Adherent tissue will be rapidly vaporised, and small tissue particles produced during vaporisation will be aspirated from the application site.

Because of its speed of debulking and side-effect configuration, the electrode unit E10 also has advantages in urological surgery as an EVAP technique for use in conjunction with a resectoscope. A resectoscope electrode unit is introduced very differently, in that is mounted on an endoscope prior to passage of the assembled instrument through a working sheath via the urethra. The proximal end of the electrode unit is connected to a trigger assembly and an electrical contact which is integral with the resectoscope. By this means, the electrode unit E1 can be moved back and forth through a defined range of motion by operating the trigger mechanism. As the electrode unit E10 is assembled prior to introduction, the size of the tip is not constrained by working channel dimensions, but rather by the diameter of the working sheath which can be up to 10 mm. Part of this diameter is occupied by the support wires to the electrode unit E10, which wires are commonly bent in a downward angle, with respect to the endoscopic image, to the working tip, so that they do not interfere with either visulation or its operation. Because of the reciprocatory movement of the rod 314, the active electrode 312 operates over a length lying within the range of from 3 mm to 4 mm and a width lying in the range of from 2 mm to 3 mm, and this size is necessary for urological surgery given that, on average, 20-30 grammes of prostate tissue must be removed.

Because of the reservoir effect of the urinary bladder, and the mounting of the endoscope to view the tip of the active electrode 312 from below, bubble generation during vaporisation is less of a problem during endoscopic urology, as the bubbles flow away from the endoscope to accumulate in the bladder. Nevertheless, the use of the electrode unit E10 substantially reduces the possibility of bubble generation causing problems.

Although the electrode unit E10 is intended primarily for use in the vaporisation of tissue it can also be used for desiccation, particularly of synovial membranes or to separate muscle attachments. In this case, once the electrode assembly of the electrode unit E10 has been introduced into a selected operation site, the RE generator 1 is actuated using the footswitch 5a or the push button 7a. The generator I will then provide sufficient RF power to the electrode assembly to maintain the saline adjacent to the active electrode 312 substantially at its boiling point without creating a vapour pocket surrounding that electrode. The instrument can then be manipulated by moving the active electrode 312 across the surface of the tissue to be treated in a side-to-side "painting" technique.

The electrode unit E10 can also be used for delivering a blended power output. This is achieved by automatically alternating the output of the RF generator 1 between the desiccation and vaporisation power levels, more haemostasis being produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

The active electrode 312 of the unit E10 is a side effect electrode (i.e. its treatment axis is peroendicular to the shaft). Axial agitation is advantageous with such electrodes, in that the entire electrode can be brought into contact with tissue. As a result, the exposed area can be made very small, allowing operation at lower powers and less at higher saline flow rates.

Figure 16:
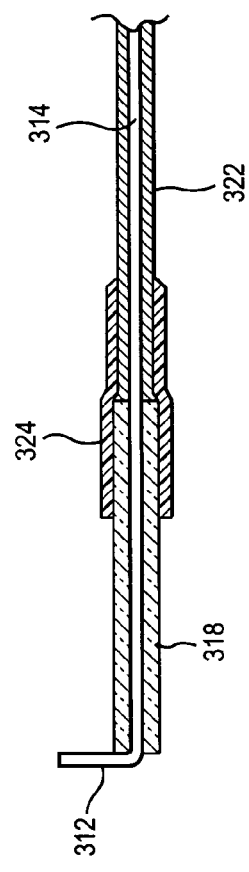
FIG. 16 is a diagrammatic side elevation of the electrode assembly of the electrode unit of FIG. 15.
Figure 17:
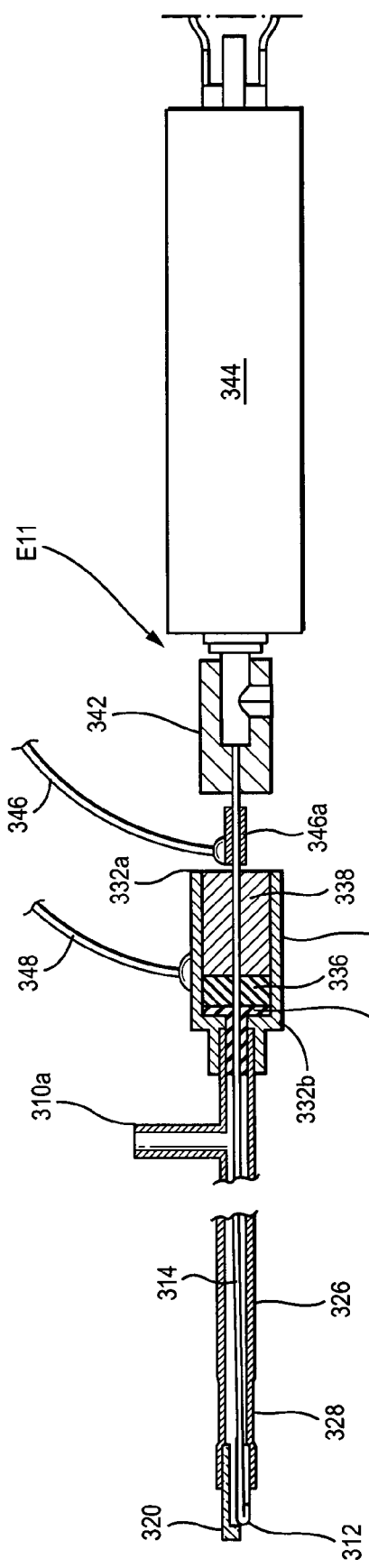
FIG. 17 is a diagrammatic side elevation, partially broken away, of a second form of electrode unit constructed in accordance with the invention.
Figure 18:
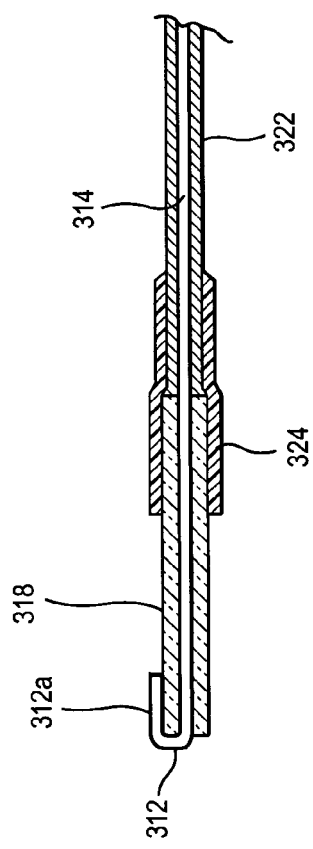
FIG. 18 is a diagrammatic side elevation of the electrode assembly of the electrode unit of FIG. 17.

FIGS. 17 and 18 show the second form of electrode unit E11. This instrument is a modification of that shown in FIGS. 15 and 16, and so like reference numerals will be used for like parts, and only the modifications will be described in detail. There are two main modifications, the first being to the drive to the rod 314, and the second to the configuration of the active electrode 312.

In the first modification, the motor 344 rotatably drives the rod 314 via a coupling assembly 342. As with the embodiment of FIGS. 15 and 16, the rod 314 passes through aligned apertures in the washer 334, the gland 336 and the delrin bush 338. The bush 338 is somewhat longer than the equivalent bush of the embodiment of FIGS. 15 and 16 extending to the end 332a of the sleeve 332. A slip ring 346a is provided to connect the connector 346 to the rod 314.

The other main modification is that the active electrode 312 (the free end of the tungsten rod 314—in this embodiment of 0.5 mm diameter) is bent back over the free end of the ceramic tube 318. The turned-back portion 312a of the electrode 312 constitutes a side effect electrode. An apertured region 320a is formed between the ceramic tip 320 and the active electrode 312, this region loading to the aspiration channel defined by the interior of the shaft 310.

Another modification is that the rod 314 is a flexible drive rod whose distal end portion is off-set with respect to the central longitudinal axis of the shaft 310. In use, when the generator 1 is turned on, the motor 344 begins to rotate, causing the rod 314 to rotate within the shaft 310. This rotation provides a mechanical agitation that is sufficient to dislodge any sublimation products which condense within the shaft. The off-set of the rod 314 results in an unstable oscillation being set up in the rod, which sweeps adherent tissue debris from the inner wall of the shaft 310.

Figure 19:
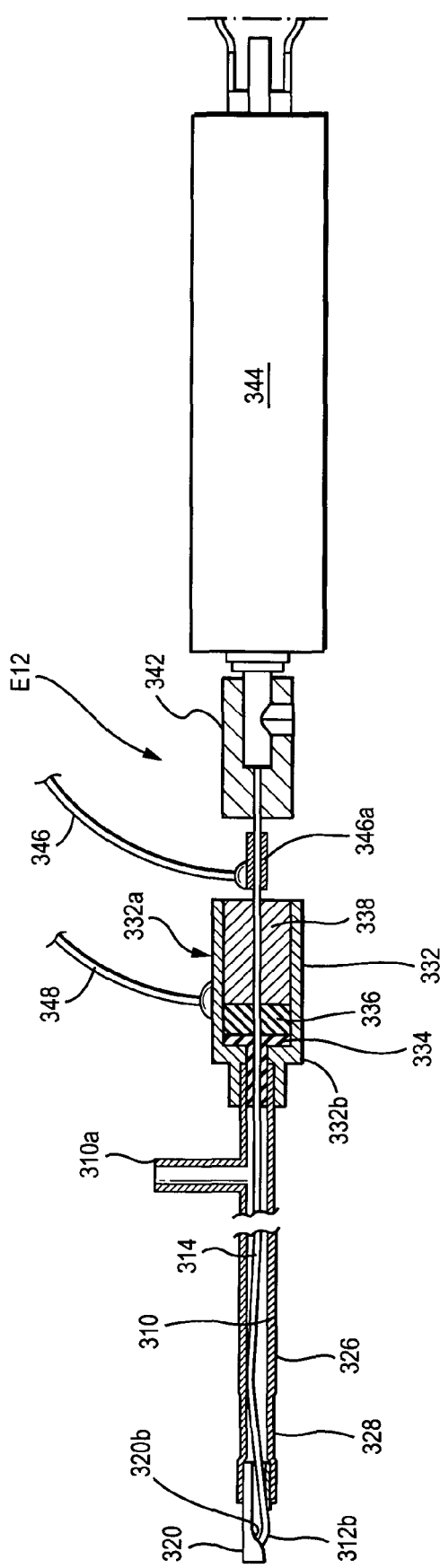
FIG. 19 is a diagrammatic side elevation, partially broken away, of a third form of electrode unit constructed in accordance with the invention.
Figure 20:
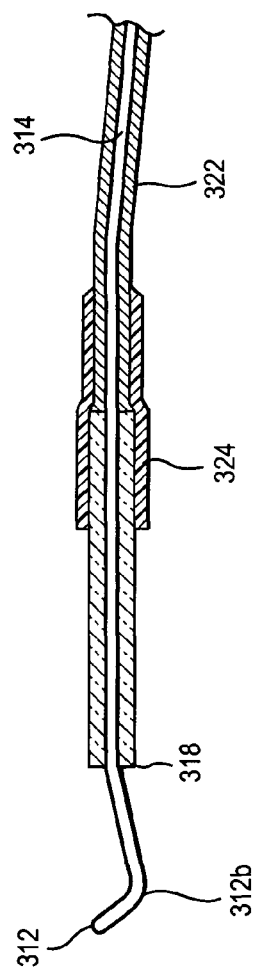
FIG. 20 is a diagrammatic side elevation of the electrode assembly of the electrode unit of FIG. 19.

FIGS. 19 and 20 show the third form of electrode unit E12. This unit E12 is a modification of the unit E11, so like reference numerals will be used for like parts, and only the modifications will be described in detail. The main modification is to the configuration of the active electrode assembly. Thus, as shown in FIG. 20, the active electrode 312 is shaped like a crank handle, and defines an elbow 312b which is off-set from the axis of the ceramic tube 318. The ceramic tip 320 is formed with an inclined cam surface 320b which, in use, engages with the elbow 312b to force the tip of the active electrode 312 outwardly, and to ensure better tissue engagement. This crank handle configuration of the active electrode 312 also ensures that, as the tip rotates, the elbow 312b is pushed around the inner surface of the ceramic tip 320, thereby removing debris which would otherwise tend to build up there.

Figure 21:
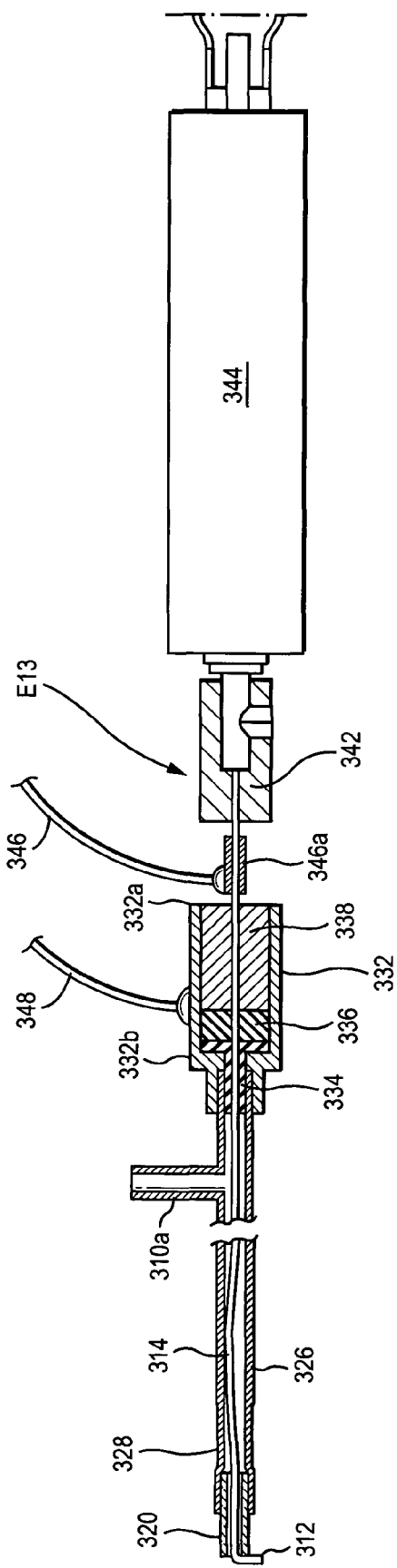
FIG. 21 is a diagrammatic side elevation, partially broken away, of a fourth form of electrode unit constructed in accordance with the invention.
Figure 22:
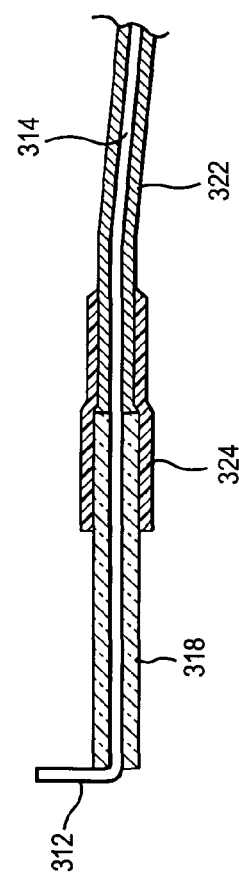
FIG. 22 is a diagrammatic side elevation of the electrode assembly of the electrode unit of FIG. 21.

FIGS. 21 and 22 show the fourth form of electrode unit E13. This unit E13 is also a modification of the unit E11, so like reference numerals will be used for like parts, and only the modifications will be described in detail. Here, the main modification is to the configuration of the active electrode 312 which, in this case, is an end effect electrode, being constituted by a simple hook-shaped end portion 312a at the end of the rod 314.

As with the embodiments of FIGS. 17 and 18, the rod 314 is a flexible drive rod whose distal end portion off-set with respect to the central longitudinal axis of the shaft 310.

As has already been described, the adherence of tissue over the active electrode 312 may induce a steady state condition, and the aspiration method must allow for removal of unvaporised tissue particles whilst not quenching vapour pocket formation. Rotation of the active electrode 312 of the electrode units E11 to E13 provides several advantages to overcome these performance issues. Thus, rotating the active electrode 312 increases the effective size of the electrode, as far as tissue contact area is concerned, for one complete rotation, whilst reducing the physical size of the active electrode. Reducing the size of the active electrode 312 reduces the vaporisation power threshold to a degree sufficient to enable aspiration along the axis of rotation when the generator control method is employed.

The introduction of rotation and aspiration through the active electrode 312, or more accurately through a channel within the range of motion of the active electrode, prevents the steady state being reached, and so prevents tissue bridging. This is achieved as tissue temporarily obstructing the aspiration channel is always treated, as opposed to positioning aspiration channels outside the range of motion of the active electrode 312, in which case only tissue adjacent to that obstructing the aspiration channel would be treated.

Given that the aspiration channel is required to cope with unvaporised tissue, the active electrode 312 is only required to incise the tissue such that the tip of the tissue in the aspiration channel is detached from the body of the tissue and then aspirated through the channel. Ideally, the truncated portion of tissue is also morcellated or partially vaporised by the active electrode 312 to reduce the size of tissue pieces. This morcellation is accomplished by introducing an off-set in the drive shaft/connector to the active electrode 312 which rotates in the aspiration channel of larger internal diameter than the external diameter of the connector, a feature which has additional advantages in preventing blocking of the aspiration channel, as is described below.

The relative contributions of tissue incision or morcellation and tissue vaporisation to the overall tissue debulking process can be controlled by the interaction of the bore of the terminal aspiration channel, the suction pressure and the bulk of the active electrode 312. Owing to the overall size constraints on the external diameter of the instrument it is, in general, the diameter of the drive rod 314 whose distal tip forms the active electrode 312 and which, therefore, also provides the means of electrical connection to the active electrode, which determines whether tissue removal occurs primarily by incision/morcellation or vaporisation. Typically a drive rod 314 (and hence active electrode 312) formed from 0.2-1.0 mm diameter tungsten wire provides incision/morcellation, and a drive rod active electrode formed from 0.5 mm diameter tungsten wire primarily provides vaporisation. The incision/morcellation technique has advantages when dealing with soft friable tissue, whereas the vaporisation technique has advantages when application is made to dense fibrous or cartilaginous tissue. The design can, therefore, be optimised for the type of tissue encountered during use in particular surgical specialties or, alternatively, a multi functional design with a drive rod and active electrode typically formed from 0.4-0.6 mm tungsten can be used.

For all four electrode units E10 to E13, agitation within the aspiration shaft 310 significantly reduces the risk of blockage, either by morcellated tissue, sublimated products of vaporisation or both. This can be accomplished by axial or rotary motion of the rod 314 which is positioned within the aspiration channel, with or without other means of fluid agitation, including the cycling of suction pressure, which may be provided as an integral feature of generator output, control of suction, and sonic pressure waves. To enhance the effect of agitation, it is beneficial to construct the drive rod 314 from a lubricious material to reduce adherence.

Each of the electrode units E10 and E13, has the additional advantage that the aspiration in the region of the active electrode 312 restricts the flow of convection currents in the saline surrounding the electrode assembly. As the power threshold required to reach vaporisation is dependent on the power dissipation of the active electrode 312 and the flow characteristics around it, the power threshold is dependent upon the maximum rate of convection. Consequently, the restriction of the convection currents reduces the power threshold and/or permits the use of higher saline flow rates, and this is advantageous as it enables the use of a cheaper RF generator, as well as avoiding problems such as dissipation within the instrument, and catastrophic overheating of the active electrode. It also facilitates control of the generator once vaporisation commences. The importance of power threshold of vaporisation is discussed in greater detail in the specification of our International Patent Application No.GB97/00065.

Moreover, each of the electrode units E10 to E13 is such as to prevent tissue bridging, as the tendency for tissue to obstruct the aspiration channel is, in each case, obviated by the movement of the active electrode ensuring that such tissue is treated. The movement of the active electrode 312 also ensures tissue morcellation, though this is effected by electrosurgery rather than by mechanical cutting.

It is a feature of each of the electrode units E10 to E13 that pieces of morcellated tissue separated from a surgical site will be drawn into the aspiration channel by the suction pressure. Should such pieces be too large to enter the aspiration channel, they will be reduced in size by a combination of the mechanical action of the agitated electrode 312 and the electrosurgical action created by the positioning of the return electrode 328 in relation to the aspiration channel. In the limit, the spacing of the return electrode 328 relative to the motion of the agitated electrode 312 can be adjusted to allow a controlled level of periodic arcing between the two. This aspect permits control of the relative strength of the mechanical and electrosurgical actions in keep the aspiration channel clear. This aspect is described in greater detail in the specification of our British Patent Application.

It will be apparent that modifications could be made to the electrode units described above. For example, instead of providing an off-set drive rod 314, this rod could be loosely coiled so that the coils lie against the inner wall of the aspiration channel, whereby, during rotation, a worm screw action occurs to encourage proximal movement of tissue debris, as well as cleaning of the inner wall of the channel.

The motor 344 of each of the embodiments would be powered by the RE generator 1. This has the advantage that the motor 44 can be controlled by means that require the RF output voltage to exceed the vaporisation power threshold before sufficient power is delivered to energise the motor. Control means for the purpose could be mounted with the motor 344 within the handpiece 3.

It would also be possible to introduce axial motion during rotation. Thus, for the electrode unit E13, the simple 90° hook form active electrode 312 can rotate on a bearing surface provided by the distal end face of the ceramic tube 318, this end face being provided with ratchet teeth features. Thus, as the rod 314 rotates, the hook-shaped end portion 312a moves in and out as it engages and disengages the ratchet teeth, this axial movement being permitted by the off-set flexible drive rod 314 repeatedly elongating and shortening.

As an alternative to an electric motor, each of the units E10 to E13 could be powered by a fluid drive generated through a rotary vane or similar apparatus, which, in turn, may be powered by the suction means.

It is also possible to power the rotary drive by the RF generator 1, so that an integral and interactive system of the rotary drive, the active electrode 312, the RF generator and the suction means is provided.

The upper limit of the speed of rotation of the units E11 to E13 is defined at that level which elevates the vaporisation power threshold beyond the output range of the RF generator 1, which will, in turn, be dependent upon the geometry of the active electrode 312. Typically, the speed of tissue removal is increased with increased rotary speed when primarily employing the incision/morcellation technique, and is increased with decreased rotary speed when primarily employing the vaporisation technique. It is, therefore, evident that, in a multi-functional design, it is advantageous for the user to vary the rotary speed depending on the nature of the tissue being treated. To this end, a typical range of rotary speeds would be from 100 revs/min to 1000 revs/mn.

With the rotary action electrode units E11 to E13, the effective size of the active electrode 312 is increased, and a significant aspect is the incision of tissue. The active electrode 312 is fabricated from the distal end of the drive rod 314, so simple wire form electrodes meet these performance requirements. The only drawback of these simple electrode forms is that asymmetry of the tissue contact can make it difficult to maintain an accurate location on a tissue surface, particularly when that surface is comprised of more fibrous or more dense tissue.

If the wire form active electrode 312 protrudes from the ceramic tube 318, for example in a simple loop form as with the electrode unit E11, then the potential exists for the loop to excise tissue pieces too large for aspiration through the distal opening of the aspiration channel. Should this occur, the exposed distal end of the drive rod 314 within the aspiration channel performs an important function in morcellating and vaporising such tissue pieces, so that they are reduced in size sufficiently to enter the aspiration channel. This function is enhanced by the eccentric motion of the drive rod 314 within the aspiration channel.

Whilst the amount of protrusion of the active electrode 312 from the distal end of the ceramic tube 318 is governed by the rules described in our International Patent Application GB96/01473, the effect of aspiration in increasing vaporisation threshold changes these rules. The other performance factor governing the dimension of the active electrode 312 is similar to that defining the diameter of the wire. Thus, the thinner wire forms, which are used on soft tissue, can protrude from the distal end of the ceramic tube 318 in the treatment axis; whilst the thicker wire forms, which are used on more dense tissue, ideally extend beyond the distal end of the ceramic tube in the treatment axis by an amount not exceeding the diameter of the wire.

The active electrode 312 may also take on more convoluted or more complex generally planar forms of end effect electrodes and generally axial forms for side effect electrodes, for example coils, spirals. meshes or multiple spokes.

Our International Patent Application GB96/01472 describes a technique of introducing a conductive fluid to the region of a tissue treatment (active) electrode in order to define, in use, a conductive fluid path between the active electrode and a return electrode. The electrode units E10 to E13 of the present invention could be modified to incorporate those features. In particular, these units could be modified for use in gaseous operating environments, either on the surface of a body or within body cavities.

The specification of our British Patent Application 9612993.7 describes a technique of aspiration in the vicinity of a tissue treatment (active) electrode, wherein the suction pressure is controlled by generator output features in order to facilitate vaporisation by intermittently lowering the vaporisation threshold by cessation of suction flow. The techniques could advantageously be incorporated in the electrode units E10 to E13, both to ensure the vaporisation threshold is exceeded between suction pulses, and as a result of the suction pulsing assisting in preventing blockage of the aspiration channel.

As a suction pulse is initiated only once the vaporisation threshold has been exceeded, tissue can only be attracted to the active electrode once the threshold is exceeded by activation remote from the tissue within the surrounding distension medium. It is known that the vaporisation threshold is lowered once tissue is engaged by the active electrode. It is, therefore, advantageous for suction to be applied initially without RF activation as a variable time delay feature.

In summary the electrosurgical instrument of the invention has the following advantageous features:—

1. A small active electrode surface which is able to treat large tissue areas by virtue of active electrode movement.
2. A small active electrode to enable vaporisation, despite the cooling effects created by aspiration.
3. A mechanical movement at the active electrode tip, compatible with material removal within the aspiration channel.
4. Aspiration operation is dependent upon the vaporisation condition.
5. At least the outside of the shaft 310 is coated with a non-stick material such as polytetrafluoroethylene— ideally the inside of the shaft as well.
6. Active electrode tip movement occurs across the face of the aspiration channel, so that any lodged tissue is electrosurgically morcellated.
7. Active electrode agitation is dependent upon the vaporisation condition.
8. Discontinuities within the agitator rod ensure that the internal surfaces of the shaft are cleaned; or the rod flexes sufficiently to create the same effect.
9. A ceramic-to-ceramic interface at the active electrode tip ensures that the internal circumference of the outer ceramic is wiped by the inner ceramic.
10. The agitator rod is independently insulated in ceramic at its tip.
11. Offset rotary action for a side-effect electrode to enable flat surface engagement.

Figure 23:
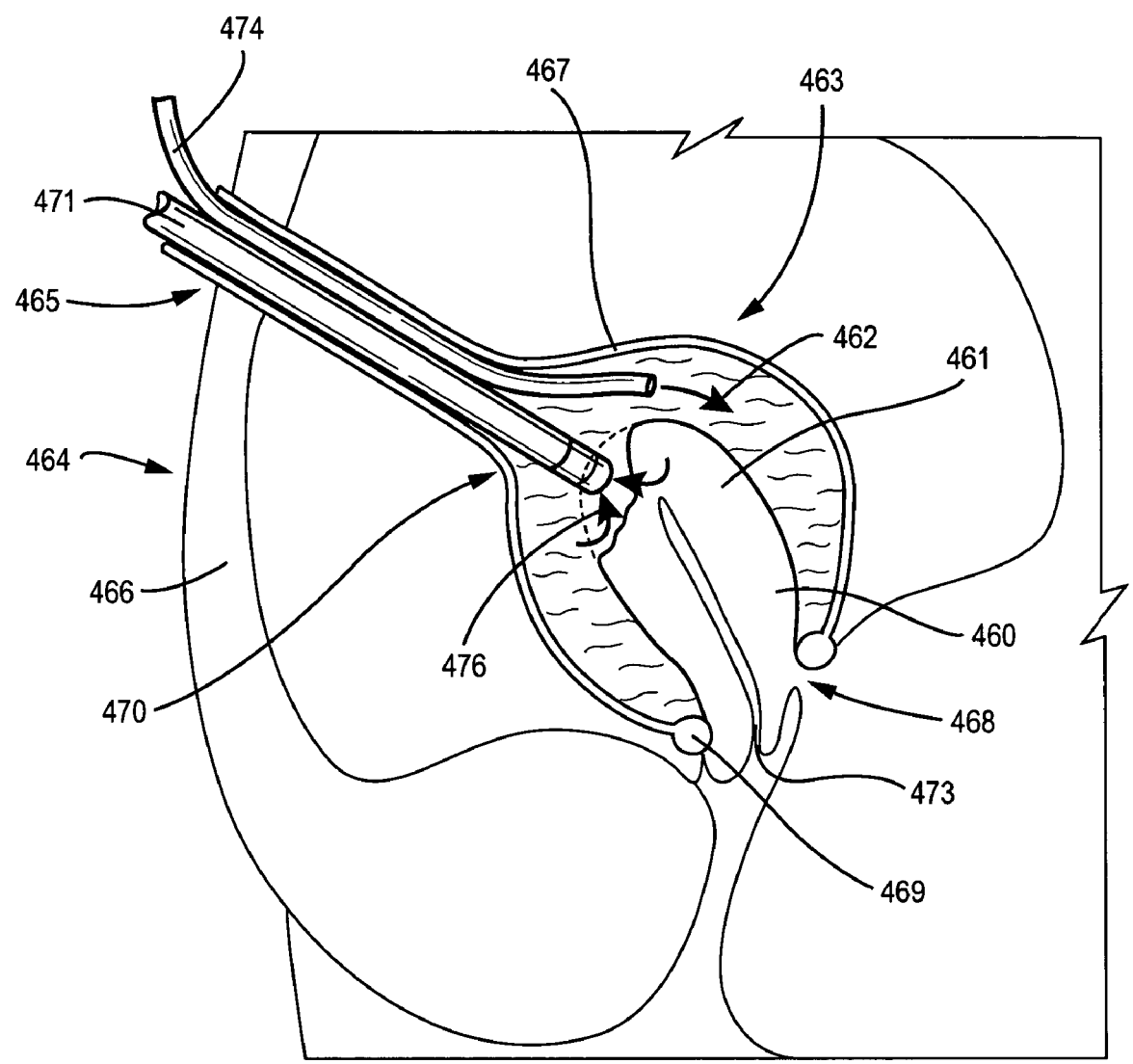
FIG. 23 is a diagrammatic representation of a sagittal cross section of a female pelvis with a fluid isolation enclosure and electrode assembly in position to extract the uterus by a process of endoscopic electrosurgical morcellation.

The present invention further includes a system and method for removing tissue, such as a uterus, from within a natural body cavity using a fluid enclosure. FIG. 23 is a diagrammatic representation of a sagittal cross section of the female pelvis with the fluid isolation enclosure and electrode assembly in position to extract the uterus by a process of endoscopic electrosurgical morcellation.

Referring to FIG. 23, fluid enclosure 467 is inserted through a second trocar (not shown) into the other side of peritoneal cavity 463 of patient 464 from the first trocar (not shown) in a deflated condition using the rigidity of the collapsed loop 469. Both trocar sites are used prior to deployment of fluid enclosure 467 for the insertion of instruments, such as cutting forceps disclosed in U.S. Pat. No. 5,445,638 to Rydell to surgically divide the lateral support tissues and vessels of the uterus. Upon insertion, proximal open end 470 of enclosure 467 for the insertion of electrosurgical instrument 471 is within the peritoneal cavity 463. The balance of fluid enclosure 467 is then manipulated within peritoneal cavity 463 using the rigidity of loop 469, assisted by a laparoscopic grasper (not shown) inserted through the first trocar. Loop 469 and enclosure 467 are maneuvered over fundus 461 of uterus 460 and ultimately the uterocervical or uterine cervix junction 473, whereby fundus 461 is completely enclosed within fluid enclosure 467. Loop 469 is then tightened around uterine cervix junction 473. The proximal end 470 of fluid enclosure 467 is then grasped using the laparoscopic grasper and delivered through the first trocar ready for insertion of the electrosurgical instrument 471, after which enclosure 467 is inflated using a conductive fluid, such as saline (see in-flow arrow 462 in FIG. 23) delivered to fluid enclosure 467 using a tube 474 inserted into the proximal open end 470 of fluid enclosure 467. Loop 469 effectively forms a pressure seal against the uterine cervix junction 473 to contain the conductive fluid used to fill fluid enclosure 467. The pressure exerted by the fluid filling enclosure 467 is partially controlled by a pump (not shown) connected to enclosure 467 via tube 474. It is further controlled by the amount of fluid sucked out by instrument 471 (see out-flow arrows 476 in FIG. 23). As shown in FIG. 21, instrument 471 has a shaft 310 with a hollow interior connected to a transverse tubular member 310*a* which is connected to a suction pump (not shown), and so constitutes a suction/exhaust port.

Also inserted into the proximal open end 470 of fluid enclosure 467 is electrosurgical instrument 471 for removing the fundus 461 of uterus 460. Electrosurgical instrument 471 is connected to an electrosurgical generator (not shown), which generates a radio frequency oscillating voltage output across first and second output terminals. Preferably, electrosurgical instrument 471 has a tissue treatment electrode connected to the first generator output terminal, and a return electrode connected to the second generator output terminal, the return electrode being spaced away from the treatment electrode along the longitudinal axis of the electrosurgical instrument.

To remove tissue from fundus 461 and body 460 of the uterus at a high rate, an electrosurgical generator with a high level peak-to-peak voltage output can be used. An example of such a generator is disclosed in U.S. Pat. No. 6,228,081, the entire contents of which are incorporated herein by reference. To permit a higher rate of electrosurgical tissue removal, the '081 patent generator produces a pulsed radio frequency output signal having a peak-to-peak voltage of between 600 to 1,250V with a 50% duty cycle. In practical application, such a generator would preferably produce a pulsed radio frequency output signal with a peak-to-peak voltage of between 600 to 1,250V. Preferably, the generator would also be used with an electrode temperature sensing arrangement that reduces the duty cycle of the pulsed radio frequency output signal when the temperature of the electrode reaches a predetermined level to avoid destruction of the electrosurgical instrument.

An endoscope (not shown) is used throughout the procedure to visualize the inside of the peritoneal cavity 463 of patient 464. The endoscope is inserted through a third trocar (not shown) immediately adjacent to the umbilicus of patient 464. The morcellation and removal of the uterus from within the fluid enclosure 467 may be viewed from outside the enclosure, should such enclosure be constructed of a translucent material. Alternatively, the endoscope may be inserted into the fluid enclosure 467 to view the procedure directly through either the proximal open end 470 of fluid enclosure 467 or a second proximal opening (not shown) in enclosure 467. In the latter case, the second proximal opening may be grasped similarly to the proximal open end 470 using a laparoscopic grasper, whereupon when the endoscope is delivered through the third trocar it may be inserted into the fluid enclosure 467 to view the procedure directly.

Upon insertion, electrosurgical instrument 471 is then manipulated under endoscopic visualization through proximal end 470 to cut and vaporize tissue comprising fundus 461 and body 460. For this purpose instrument 471 includes an active electrode 312, which is an end effect electrode constituted by a simple hook-shaped end portion 312*a* at the end of rod 314, as shown in FIG. 21.

The tissue of fundus 461 and body 460 is cut and vaporized using instrument 471, and then removed from fluid enclosure 467. For this purpose, as noted above, the shaft 310 of instrument 471 includes a hollow interior that is connected to transverse tubular member 310*a*, which, in turn, is connected to a suction pump for removing by suction both the conductive fluid that has been delivered by tube 474 and the tissue pieces of fundus 461 and body 460 that have been cut and vaporized. The oscillation of active electrode 312 of instrument 471 ensures that tissue pieces removed electrosurgically by vaporisation from an operation site are morcellated electrosurgically by the oscillating electrode, thereby preventing large tissue pieces bridging the aspiration channel. Fundus 461 and body 460 of the uterus is thus removed to the level of the uterocervical junction around which loop 469 was positioned.

Although the present invention has been described in terms of particular embodiments, it is not intended that the invention be limited to those embodiments. Modifications of the embodiments within the spirit of the invention will be apparent to those skilled in the art. The scope of the invention is defined by the claims that follow.

What is claimed is:

1. An electrosurgical system comprising:
   a radio frequency generator,
   an electrosurgical instrument, and
   a fluid enclosure within a natural body cavity of a patient,
   the fluid enclosure being sealed around a portion of a patient's body within the cavity which is to be removed and containing an electrically-conductive fluid surrounding the portion of the patient's body to be removed,
   the generator having a radio frequency output for delivery of power to the electrosurgical instrument when immersed in the electrically-conductive fluid,
   the electrosurgical instrument having an electrode assembly at the distal end thereof, the electrode assembly comprising a tissue treatment electrode and a return electrode longitudinally spaced therefrom so that, in use, the conductive fluid completes an electrical circuit between the tissue treatment electrode and the return electrode,
   wherein the fluid enclosure includes at least one open end through which the electrosurgical instrument is insertable into the fluid enclosure, and through which the electrically-conductive fluid is inserted and removed from the enclosure.

2. An electrosurgical system according to claim 1 wherein the fluid enclosure includes a distal open end surrounded by an adjustable loop that can be tightened and a proximal open end for inserting the electrosurgical instrument into the fluid enclosure.

3. An electrosurgical system according to claim 2 wherein the loop is a resilient band extending around the edge of the distal open end.

4. An electrosurgical system according to claim 2 wherein the loop is a drawstring arrangement that can be tightened and released.

5. An electrosurgical system according to claim 1 wherein the tissue treatment electrode has at least a portion extending laterally with respect to a longitudinal axis of the electrosurgical instrument.

6. An electrosurgical system according to claim 5 wherein the electrosurgical instrument includes means for rotating the tissue treatment electrode with respect to the longitudinal axis.

7. An electrosurgical system according to claim 1 wherein the electrosurgical instrument includes a shaft with a hollow interior connected to a transverse tubular member which is connected to a suction pump so as to constitute a suction/exhaust port.

8. An electrosurgical system according to claim 1 wherein the tissue treatment electrode includes a hook-shaped end portion located at the end of a rod.

9. An electrosurgical system according to claim 1 wherein the generator produces a pulsed radio frequency output signal having a peak-to-peak voltage of about 600V to 1,250V and a duty cycle of about 50%.

10. An electrosurgical system according to claim 2 further comprising an endoscope that is inserted through the proximal open end of the fluid enclosure into the fluid enclosure.

11. An electrosurgical system according to claim 2, wherein the fluid enclosure includes a second proximal opening for insertion of an endoscope into the fluid enclosure.

12. An electrosurgical system comprising:
a radio frequency generator,
an electrosurgical instrument, and
a sealing means,
the generator having a radio frequency output for delivery of power to the electrosurgical instrument when immersed in an electrically-conductive fluid,
the electrosurgical instrument having a longitudinal axis and an electrode assembly at the distal end thereof, the electrode assembly comprising a tissue treatment electrode and a return electrode spaced therefrom so as to define, in use, a conductive fluid path that completes an electrical circuit between the tissue treatment electrode and the return electrode,
wherein the sealing means is adapted to create a fluid enclosure within a natural body cavity such that a portion of a patient's body which is to be removed is within the fluid enclosure, and wherein the sealing means includes at least one port through which the electrosurgical instrument is insertable, and through which the electrically-conductive fluid can enter and/or leave the enclosure.

13. An electrosurgical system according to claim 12 wherein the tissue treatment electrode has at least a portion extending laterally with respect to the longitudinal axis of the electrosurgical instrument.

14. An electrosurgical system according to claim 12 wherein the instrument includes means for rotating the tissue treatment electrode with respect to said longitudinal axis.

15. An electrosurgical system according to claim 12 wherein the return electrode is axially spaced from the tissue treatment electrode in the direction of the said longitudinal axis.

16. An electrosurgical system according to claim 12 wherein the sealing means includes a distal open end surrounded by an adjustable loop that can be tightened and a proximal open end that is the at least one port for inserting the electrosurgical instrument into the fluid enclosure.

17. An electrosurgical system according to claim 16 wherein the loop is a resilient band extending around the edge of the distal open end.

18. An electrosurgical system according to claim 16 wherein the loop is a drawstring arrangement that can be tightened and released.

19. An electrosurgical system according to claim 12 wherein the electrosurgical instrument includes a shaft with a hollow interior connected to a transverse tubular member which is connected to a suction pump so as to constitute a suction/exhaust port.

20. An electrosurgical system according to claim 12 wherein the tissue treatment electrode includes a hook-shaped end portion located at the end of a rod.

21. An electrosurgical system according to claim 12 wherein the generator produces a pulsed radio frequency output signal having a peak-to-peak voltage of about 600V to 1,250V and a duty cycle of about 50%.

22. An electrosurgical system according to claim 21 further including an electrode temperature sensing arrangement that reduces the duty cycle of the pulsed radio frequency output signal when the temperature of the tissue treatment electrode reaches a predetermined level.

23. An electrosurgical system according to claim 16 further comprising an endoscope that is inserted through the proximal open end of the fluid enclosure into the sealing means.

24. An electrosurgical system according to claim 16, wherein the fluid enclosure includes a second proximal opening for insertion of an endoscope into the sealing means.

25. An electrosurgical system for removing tissue from within a natural body cavity, the electrosurgical system comprising:
means for enclosing, in a substantially fluid-tight manner, a space in the body cavity within which the tissue to be removed is located,
means for delivering electrically-conductive fluid to the enclosing means whereby the tissue to be removed from the body cavity is surrounded by the electrically-conductive fluid,
means for generating a radio frequency oscillating voltage output across first and second output terminals,
means manipulated within the enclosing means for electrosurgically vaporizing and morcellating the tissue to be removed from the body cavity, the electrosurgical means including:
means connected to the first output terminal for treating tissue electrosurgically,
means connected to the second output terminal for completing an electrical return path through the electrically-conductive fluid, and
means for removing from the enclosing means electrically-conductive fluid and vaporized and morcellated tissue.

26. An electrosurgical system for removing the fundus and body of a uterus from within the peritoneal cavity of a patient, the electrosurgical system comprising:
means for enclosing, in a substantially fluid-tight manner, a space in the peritoneal cavity within which the fundus and body to be removed are located,
means for delivering electrically-conductive fluid to the enclosing means whereby the fundus and body to be removed from the body cavity are surrounded by the electrically-conductive fluid, means for generating a radio frequency oscillating voltage output across first and second output terminals, means manipulated within the enclosing means for electrosurgically vaporizing and morcellating the fundus and body, the electrosurgical means including:
means connected to the first output terminal for treating tissue electrosurgically,
means connected to the second output terminal for completing an electrical return path through the electrically-conductive fluid, and
means for removing from the enclosing means electrically-conductive fluid and vaporized and morcellated uterine tissue.

27. An electrosurgical system according to claim 26 wherein the enclosing means includes a distal open end surrounded by an adjustable loop that can be tightened and a proximal open end for inserting the electrosurgical means into the enclosing means.

28. An electrosurgical system according to claim 27 wherein the loop is a resilient band extending around the edge of the distal open end.

29. An electrosurgical system according to claim 27 wherein the loop is a drawstring arrangement that can be tightened and released.

30. An electrosurgical system according to claim 26 wherein the electrosurgical means includes a shaft with a hollow interior connected to a transverse tubular member which is connected to a suction pump so as to constitute a suction/exhaust port.

31. An electrosurgical system according to claim 26 wherein the tissue treatment means includes a hook-shaped end portion for morcellating tissue.

32. A method of removing tissue from within a natural body cavity using an electrosurgical system comprising:
an electrosurgical generator for generating a radio frequency oscillating voltage output across first and second output terminals,
an electrosurgical instrument having a longitudinal axis, the electrosurgical instrument including a tissue treatment electrode connected to the first generator output terminal, and a return electrode connected to the second generator output terminal,
fluid delivery means for delivering electrically-conductive fluid to the body cavity,
the method including the steps of:
enclosing, in a substantially fluid-tight manner, a space in the body cavity within which the tissue to be removed is located, and within which at least the tissue treatment electrode is located,
operating the fluid delivery means to fill at least partly the space with electrically-conductive fluid,
operating the generator to apply a radio frequency voltage between the tissue treatment and return electrodes, and completing at least a part of a conduction path between the electrodes using the electrically-conductive fluid, and
manipulating the electrosurgical instrument in the vicinity of the tissue to be removed from the body cavity.

33. A method according to claim 27 wherein the tissue treatment electrode has at least a portion extending laterally with respect to the longitudinal axis of the electrosurgical instrument, wherein the electrosurgical instrument further comprises drive means for rotating the tissue treatment electrode about the longitudinal axis, and wherein the method further comprises the step of operating the drive means to rotate the tissue treatment electrode about the longitudinal axis.

34. A method of removing at least the fundus and body of the uterus of a patient using an electrosurgical system comprising:
an electrosurgical generator adapted to generate a radio frequency oscillating voltage output across first and second output terminals,
an electrosurgical instrument having a longitudinal axis, the electrosurgical instrument including a tissue treatment electrode connected to the first generator output terminal, and a return electrode connected to the second generator output terminal, and
fluid delivery means for delivering electrically-conductive fluid,
the method comprising the steps of:
enclosing, in a substantially fluid-tight manner, the body and fundus of the uterus of the patient, and within which at least the tissue treatment electrode is located,
operating the fluid delivery means to fill at least partly the body and fundus enclosure with electrically-conductive fluid,
operating the generator to apply a radio frequency voltage between the tissue treatment and return electrodes, and completing at least a part of a conduction path between the electrodes using the electrically-conductive fluid, and
manipulating the electrosurgical instrument to remove at least the fundus and the body of the uterus.

35. A method according to claim 34 wherein the tissue treatment electrode has at least a portion extending laterally with respect to the longitudinal axis of the electrosurgical instrument, and drive means for rotating the tissue treatment electrode about the longitudinal axis, and the method includes the additional step of operating the drive means to rotate the tissue treatment electrode about the longitudinal axis.

36. A method according to claim 34 including the further initial step of dissecting the uterus from other pelvic structures such as the ovaries, broad ligaments, and round ligaments.

37. A method for removing the fundus and body of a uterus from within the peritoneal cavity of a patient, the method comprising the steps of:
enclosing, in a substantially fluid-tight manner, a space in the peritoneal cavity within which the fundus and body to be removed are located,
delivering electrically-conductive fluid to the enclosing means whereby the fundus and body to be removed from the body cavity are surrounded by the electrically-conductive fluid,
generating a radio frequency oscillating voltage output across first and second output terminals,
using the radio frequency oscillating voltage output within the enclosure to electrosurgically vaporize and morcellate the fundus and body, and
removing from the enclosure electrically-conductive fluid and vaporized and morcellated uterine tissue.

38. A method according to claim 37 wherein the step of electrosurgically vaporizing and morcellating the fundus and body is performed using an electrosurgical means comprising means for treating tissue electrosurgically and means for completing an electrical return path through the electrically-conductive fluid to the radio frequency oscillating voltage output.

39. The method according to claim 38 wherein the step of enclosing, in a substantially fluid-tight manner, a space in the peritoneal cavity within which the fundus and body to be removed are located, is performed using an enclosing means comprising a distal open end surrounded by an adjustable loop that can be tightened and a proximal open end for inserting the electrosurgical means into the enclosing means.

40. The method according to claim 39 wherein the loop is a resilient band extending around the edge of the distal open end.

41. The method according to claim 39 wherein the loop is a drawstring arrangement that can be tightened and released.

42. The method according to claim 38 wherein the electrosurgical means includes a shaft with a hollow interior connected to a transverse tubular member which is connected to a suction pump so as to constitute a suction/exhaust port.

43. The method according to claim 38 wherein the tissue treating means includes a hook-shaped end portion for morcellating tissue.

* * * * *